(12) United States Patent
Takaki et al.

(10) Patent No.: US 10,768,119 B2
(45) Date of Patent: Sep. 8, 2020

(54) APPLICATOR, APPLICATOR SET, DEGREE OF CLEANLINESS DETERMINATION METHOD, AND DEGREE OF CLEANLINESS DETERMINATION SYSTEM

(71) Applicant: 3M INNOVATIVE PROPERTIES COMPANY, St. Paul, MN (US)

(72) Inventors: Shunsuke Takaki, Sagamihara (JP); G. Marco Bommarito, Stillwater, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 15/318,237

(22) PCT Filed: Jun. 17, 2015

(86) PCT No.: PCT/US2015/036150
§ 371 (c)(1),
(2) Date: Dec. 12, 2016

(87) PCT Pub. No.: WO2015/200065
PCT Pub. Date: Dec. 30, 2015

(65) Prior Publication Data
US 2017/0108448 A1    Apr. 20, 2017

Related U.S. Application Data

(60) Provisional application No. 62/016,813, filed on Jun. 25, 2014.

(51) Int. Cl.
*G01N 21/94*    (2006.01)
*G01N 21/88*    (2006.01)
*A61L 2/28*    (2006.01)

(52) U.S. Cl.
CPC ............... *G01N 21/94* (2013.01); *A61L 2/28* (2013.01); *G01N 21/8803* (2013.01)

(58) Field of Classification Search
CPC ........ C09D 5/008; C09D 5/004; C09D 11/16; C09D 7/40; C09D 7/65; C09D 7/66;
(Continued)

(56) References Cited

U.S. PATENT DOCUMENTS 4,312,676 A    1/1982  Hogseth
5,736,602 A    4/1998  Crocker et al.
(Continued)

FOREIGN PATENT DOCUMENTS

CN    105050684 A     11/2015
DE    196 49 925      6/1998
(Continued)

*Primary Examiner* — Mark R Gaworecki
(74) *Attorney, Agent, or Firm* — 3M IPC

(57) ABSTRACT

An applicator; an applicator set; a method for determining cleanliness of a surface using the applicator or the applicator set; and a system for determining cleanliness of a surface comprising the applicator or the applicator set. The applicator can include a marker composition and an applicator body capable of retaining the marker composition. The marker composition can include retroreflective particles and a dispersion medium, the blending ratio of the retroreflective particles being from 50 to 90 mass % on the basis of the total marker composition.

15 Claims, 18 Drawing Sheets

(58) Field of Classification Search
CPC .. C09D 7/70; A61L 2/28; B05D 5/063; G01N 21/8803; G01N 21/94
See application file for complete search history.

(56) References Cited

U.S. PATENT DOCUMENTS

| | | | |
|---|---|---|---|
| 6,623,098 B2 * | 9/2003 | Davis | B41J 2/16508 342/32 |
| 7,718,395 B2 | 5/2010 | Carling | |
| 7,780,453 B2 | 8/2010 | Carling | |
| 7,785,109 B2 | 8/2010 | Carling | |
| 8,084,410 B2 | 12/2011 | Carling | |
| 8,435,933 B2 | 5/2013 | Carling | |
| 8,639,527 B2 | 1/2014 | Rensvold | |
| 2005/0157389 A1 | 7/2005 | Shipman et al. | |
| 2006/0063856 A1 * | 3/2006 | Cordova | C09D 11/16 523/160 |
| 2007/0290865 A1 * | 12/2007 | Lynn | A61L 2/18 340/573.1 |
| 2009/0276239 A1 | 11/2009 | Swart | |
| 2012/0071376 A1 | 3/2012 | Carling | |

FOREIGN PATENT DOCUMENTS

| | | |
|---|---|---|
| DE | 197 54 717 | 7/1998 |
| JP | 2003-122823 | 4/2003 |
| JP | 4132388 | 6/2008 |
| JP | 5107633 | 10/2012 |
| JP | 5526577 | 4/2014 |
| WO | WO 1999/34240 | 7/1999 |
| WO | WO 2007/057505 | 5/2007 |
| WO | WO 2008/088424 | 7/2008 |
| WO | WO 2010/121054 | 10/2010 |
| WO | WO 2014/089387 | 6/2014 |
| WO | WO 2014/099131 | 6/2014 |
| WO | WO 2015/200063 | 12/2015 |

* cited by examiner

APPLICATOR, APPLICATOR SET, DEGREE OF CLEANLINESS DETERMINATION METHOD, AND DEGREE OF CLEANLINESS DETERMINATION SYSTEM

CROSS REFERENCE TO RELATED APPLICATIONS

This application is a national stage filing under 35 U.S.C. 371 of PCT/US2015/036150, filed Jun. 17, 2015, which claims the benefit of U.S. Provisional Patent Application No. 62/016,813, filed Jun. 25, 2014, the disclosures of which are incorporated by reference in their entirety herein.

FIELD

The present invention relates to an applicator, an applicator set, a degree of cleanliness determination method, and a degree of cleanliness determination system.

BACKGROUND

U.S. Pat. No. 7,718,395 discloses a method for the use of a transparent indicator reagent including a fluorescent substance as a method for determining whether cleaning has been sufficiently performed. This method includes a step of coating the indicator reagent on an object to be cleaned (e.g. table, chair, or the like) prior to cleaning, and a step of determining after cleaning whether or not the indicator reagent is present by sensing light emitted from the fluorescent substance due to irradiation, by ultraviolet radiation, of the object to be cleaned.

SUMMARY

Problems to be Solved by the Invention

For the determination of whether cleaning has been sufficiently performed (i.e. determination of the degree of cleanliness), it is important that the determination is possible by a simple method, that the determination is possible over a wide range, that the determination is highly accurate, and the like.

One object of the present invention is to provide an applicator, an applicator set, a degree of cleanliness determination method, and a degree of cleanliness determination system using a marker composition for which existence can be sensed over a wide range by a simple method.

Means to Solve the Problem

One aspect of the present invention is an applicator provided with a marker composition containing retroreflective particles and a dispersion medium and with an applicator body capable of retaining the maker composition, the blending ratio of the retroreflective particles being from 50 to 90 mass % on the basis of the entire amount of the marker composition.

In another aspect of the present invention, the applicator body may be porous.

In yet another aspect of the present invention, the applicator body may be capable of having interconnected cells in the interior of the applicator body.

In yet another aspect of the present invention, the cell count of the interconnected cells may be 15 to 100 cells per 25 mm.

In yet another aspect of the present invention, the applicator body may be further composed of: a retention body for retaining the applicator body so that at least part of the applicator body is exposed, and a lid body detachably attached to the retention body, for hermetically sealing the exposed part of the applicator body.

In one aspect of the present invention, an applicator set is provided that is composed of a plurality of the applicators; each applicator respectively includes: a retention body for retention of the applicator body, the retention body including a retention part retaining the applicator body so that at least part of the applicator body is exposed, including a lid part detachably attached to the retention part of another applicator, the lid part being capable of hermetically sealing the exposed part of the applicator body of another of the applicator.

In another aspect of the present invention, an applicator among the plurality of applicators may be capable of being distinguished from the other applicators.

In another aspect of the present invention, a degree of cleanliness determination method is provided that is composed of the steps of: applying the marker composition to a pre-cleaning surface to be cleaned using the applicator or applicator set described above; radiating light onto the surface to be cleaned after the surface to be cleaned is cleaned, and sensing a reflected light from the retroreflective particles; and determining a degree of cleaning of the surface to be cleaned based on the result of sensing the reflected light.

In another aspect of the present invention, a degree of cleanliness determination system is provided that is composed of: a sensing means for sensing reflected light from the retroreflective particles based on image data showing a condition in which light is radiated to a surface to be cleaned that the marker composition the is applied with the applicator or the applicator set and then cleaned; and a determination means for determining the degree of cleanliness of the surface to be cleaned based on the results of sensing the reflected light obtained by the sensing means.

With the present invention, it is possible to provide an applicator, an applicator set, a degree of cleanliness determination method, and a degree of cleanliness determination system using a marker composition for which existence can be sensed over a wide range by a simple method with good accuracy.

DETAILED DESCRIPTION

Figure 1:
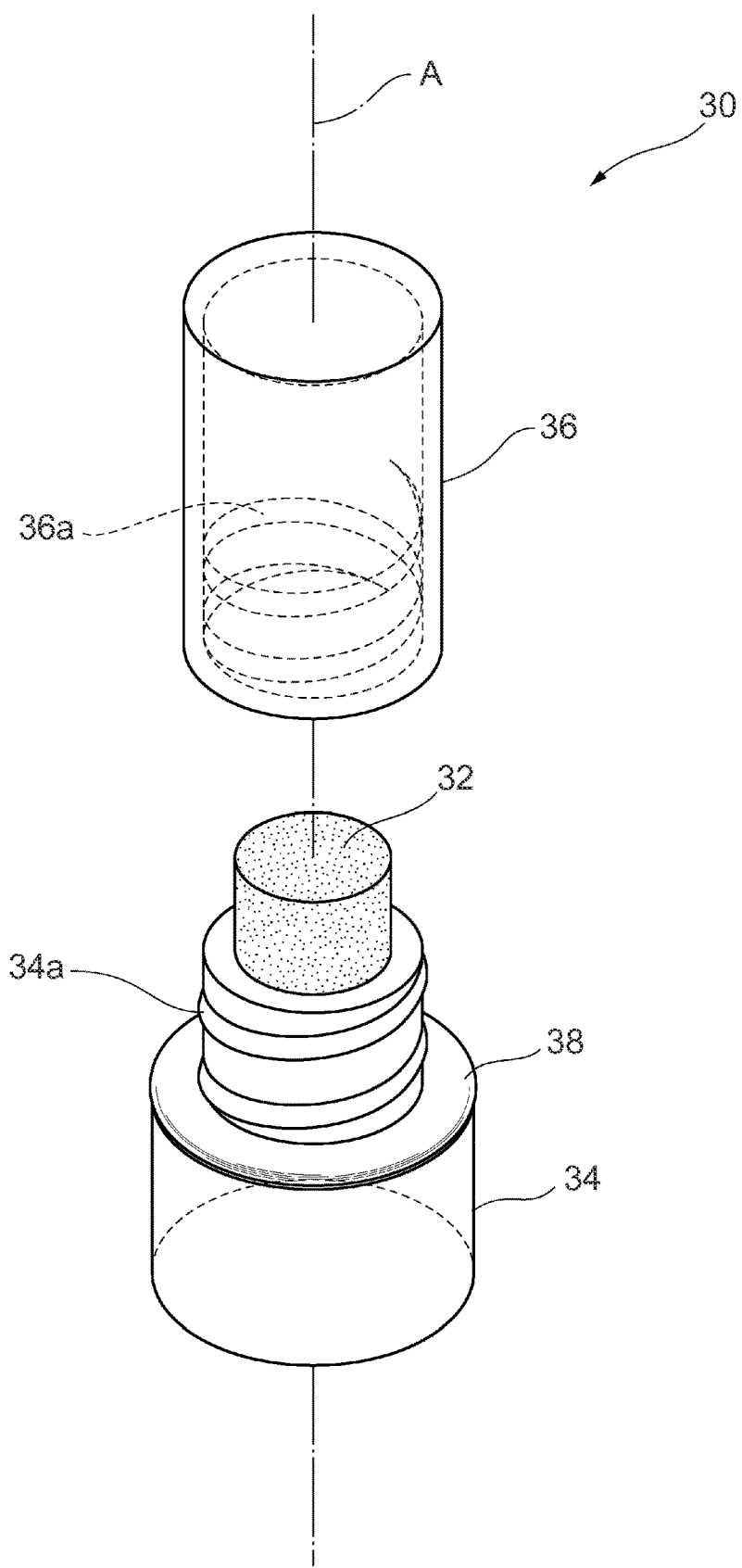
FIG. 1 is a perspective view illustrating an example of the applicator of the third embodiment.

Embodiments of the marker composition, applicator, applicator set, degree of cleanliness determination method, and degree of cleanliness determination system of the present invention will be described below in detail.

First Embodiment: Marker Composition

The marker composition of the first embodiment contains retroreflective particles and a dispersion medium, and the dispersion medium contains water and a water-soluble polymer. In addition, the blending ratio of the retroreflective particles is from 50 to 90 mass % on the basis of the entire amount of the marker composition. Here, the term "retroreflective" refers to the property of reflecting incident light back in the direction of incidence.

No particular limitation is placed on the retroreflective particles (i.e. beads) as long as the retroreflective particles display retroreflectivity. Examples of substances for use as the retroreflective particles include glass (such as soda-lime glass, borosilicate glass, and barium titanate glass) and high refractive index plastic. Glass may be used with advantage from the standpoint of reflectivity.

From the standpoints of application ability, stability, storage stability, and visibility, average particle diameter of the retroreflective particles may be set to 10 to 100 μm, 20 to 90 μm, or 30 to 80 μm. Dispersability of the retroreflective particles in the dispersion medium may be further increased when the average particle diameter of the retroreflective particles is in the aforementioned range. Moreover, the strength of reflected light from the retroreflective particles may be increased when the average particle diameter of the retroreflective particles is in the aforementioned range. Here, the expression "average particle diameter" means the average particle diameter measured according to JIS K 5600-9-3 (Testing Methods for Paints—Part 9: Coating Powders—Section 3: Particle Size Analysis by Laser Diffraction) or the like.

Particles capable of use as the retroreflective particles are exemplified by "UB-24M" and "UB-35M" (both produced by Unitika Ltd.), Beeko beads, Rambo beads, Tung beads, or the like.

From the standpoints of application ability, visibility, and reflectivity, the concentration of the retroreflective particles in the total marker composition may be 75 to 95% by weight, may be 75 to 90% by weight, or may be 75 to 85% by weight. In addition, if the dispersion medium does not contain an alcohol, the content ratio of the retroreflective particles can be set to 70 to 90 mass % or 75 to 85 mass % on the basis of the total mass of the marker composition.

The water contained in the dispersion medium is not particularly limited. In this embodiment, deionized water, distilled water, ultrapure water, or the like can be preferably used.

From the standpoint of application ability, the water content in the total marker composition is preferably 3 to 25% by weight, further preferably is 4 to 20% by weight, and most preferably is 8 to 14% by weight. If the dispersion medium does not include an alcohol, the water content in the total marker composition is preferably 9.5 to 18% by weight, more preferably 15 to 17% by weight.

The water-soluble polymer contained in the dispersion medium is not particularly limited as long as the polymer is water-soluble. Examples of water-soluble polymers include polyvinylpyrrolidone (also called "PVP" hereafter); synthetic polymers such as polyvinyl alcohol (also called "PVA" hereafter), carboxyvinyl polymers, and acrylic acid-methacrylic acid copolymers; cellulose and derivatives thereof such as methylcellulose, hydroxyethylcellulose, and carboxymethylcellulose; polysaccharides and derivatives thereof such as starch, guar gum, argininic acid salts, and mannan; gums such as xanthan gum, tragacanth gum, and guar gum; hyaluronic acid and derivatives thereof; polyglutamic acid and derivatives thereof, and substances produced by partially crosslinking these substances physically or chemically. In this specification, a water-soluble polymer that is crosslinked by subjecting polyvinylpyrrolidone to γ-ray irradiation is called "γ-ray crosslinked pyrrolidone" or "X-PVP".

From the perspectives of applicability and rapid drying, the content ratio of the water-soluble polymer may be from 3 to 20 mass %, from 4 to 10 mass %, or from 4 to 6 mass % on the basis of the total mass of the dispersion medium. In addition, the content ratio of the water-soluble polymer can be preferably set to 0.8 to 3 mass %, more preferably from 1 to 2.5 mass %, and even more preferably from 1.5 to 2.5 mass % on the basis of the total mass of the marker composition. If the dispersion medium does not contain an alcohol, the content ratio of the water-soluble polymer can be preferably set to 0.2 to 4.5 mass % and more preferably from 0.5 to 2.5 mass % on the basis of the total mass of the marker composition.

The water-soluble polymer preferably contains a polymer that is soluble in both water and an alcohol, and the dispersion medium preferably contains an alcohol. Rapid drying of the marker composition may be further improved by such a water soluble polymer and dispersion medium.

Examples of alcohols include isopropyl alcohol (also called 2-propanol; sometimes called "IPA" hereafter), ethanol, methanol, and n-propyl alcohol. In addition, examples of polymers that are soluble in both water and an alcohol include polyvinylpyrrolidone, γ-ray crosslinked polyvinyl pyrrolidone, polyvinyl alcohol, hydroxymethylcellulose, and hydroxypropyl methyl cellulose phthalate.

When the dispersion medium contains such a water-soluble polymer and an alcohol, the rapid drying of the marker composition can be further improved.

From the perspectives of applicability and rapid drying, the content ratio of the alcohol may be from 20 to 60 mass %, from 30 to 60 mass %, or from 45 to 55 mass % on the basis of the total mass of the dispersion medium. Moreover, the content of the alcohol in the total marker composition is preferably 4 to 16% by weight, further preferably is 5 to 15% by weight, and most preferably is 6 to 13% by weight.

A preferred mode of the water-soluble polymer is polyvinylpyrrolidone or γ-ray crosslinked polyvinylpyrrolidone. When these water-soluble polymers are used, the marker composition can be provided with suitable viscosity, and the adhesive strength and applicability can also be enhanced. Therefore, with the marker composition of this aspect, it is possible to achieve even better retention ability, and the phenomenon in which the marker composition droops down when applied to a ceiling or a wall surface, for example, can be reliably suppressed.

The marker composition of this embodiment may further contain a moisturizer in addition to retroreflective particles and a dispersion medium. It is possible by this means to suppress evaporation of the marker composition, and it is possible to increase storage stability of the marker composition.

Examples of moisturizers include glycerin, propylene glycol, protein, mucopolysaccharide, collagen, and elastin.

The concentration of the humectant in the total marker composition is preferably 0.1 to 2% by weight, further preferably is 0.5 to 1% by weight, and most preferably is 0.7 to 0.8% by weight. In addition, if the dispersion medium does not contain an alcohol, the content ratio of the moisturizer can be preferably set to 0.3 to 7.5 mass % and more preferably from 0.5 to 5 mass % on the basis of the total mass of the marker composition.

The marker composition of this embodiment may further contain a pH adjusting agent in addition to retroreflective particles and a dispersion medium. This makes it possible to adjust the solubility of the polymer compound contained in the dispersion medium and to increase the applicability of the marker composition.

Examples of pH adjusting agents include sodium hydroxide, potassium hydroxide, sodium carbonate, and potassium carbonate.

The marker composition of this embodiment may further contain other additives (plasticizers, moisturizers, surfactants, preservatives, or the like) within a scope that does not diminish the essence of the present invention.

The viscosity of the components excluding the retroreflective particles from the marker composition (mixture of components if there are two or more types of such components) at 25° C. may be from 2,000 to 100,000 cps, from 4,000 to 80,000 cps, or from 6,000 to 60,000 cps. Adhesive strength and application ability of the marker composition may be improved by having viscosity in the aforementioned range. Here, "viscosity" refers to the viscosity measured in a 25° C. environment in accordance with JIS Z 8803 using a B type viscometer (produced by Tokyo Keiki Inc., model BL).

The marker composition of the present embodiment may be obtained by mixing the retroreflective particles, water, the water soluble polymer, alcohol as necessary, and further additives such as a moisturizer as necessary. No particular limitation is placed on the order of blending of these components, and for example, all the components may be fed to into a vessel and then blended, or alternatively, after blending of part of the components, the other components may be added and blended in the mixture. The preferred method of preparation is exemplified by a method composed of a step of obtaining the dispersion medium by firstly blending the components included in the dispersion medium, and then a step of obtaining the marker composition by adding and blending the retroreflective particles in the dispersion medium. The processing conditions of each of these steps may be selected appropriately. Furthermore, an additive such as a humectant or the like may be added during preparation of the dispersion medium, or alternatively, the additive may be added to the dispersion medium together with the retroreflective particles, or after addition of the retroreflective particles.

Moreover, an example of the method of preparing the dispersion medium in a case in which alcohol is used is a method including a first step of mixing water and a water-soluble polymer in a hermetically sealed vessel for flammable solvents and a second step of adding and mixing alcohol into the mixture obtained in the first step.

According to the marker composition of the present embodiment, it becomes possible to sense the presence or absence of the marker composition over a wide range by a simple method with good accuracy.

That is to say, the aforementioned marker composition is able to stably retain the retroreflective particles in the dispersion medium, and is able to be readily applied over a wide range. Moreover, after application, the marker composition may be readily removed from the application region by wiping using a cleaning article (i.e. cloth, mop, or the like) including water or a mixed liquid of water-alcohol or the like. Furthermore, during application and removal of the marker composition, the marker composition is illuminated by light as natural lighting or indoor lighting. However, since the line of sight of the person holding the cleaning article and cleaning the cleaning region is normally different from the direction of incidence and reflection of light, the person holding the cleaning article and cleaning the cleaning region is normally unable to visually sense reflected light from the retroreflective particles.

Then when light is used to illuminate the aforementioned marker composition, such light is reflected toward the light source irrespective of the position of incidence of light on the particle surface (i.e. irrespective of the incidence angle of light). Thus reflection may be detected from a wider range of incident angles in comparison to specular reflection and scattered reflection, and it is possible to increase the intensity of the detected reflected light. Furthermore, the illuminating light may be any type of light that indicates that the retroreflective particles are retroreflective. Thus in comparison to the case of coating the application region with an ultraviolet radiation fluorescing substance and then illuminating the application region with ultraviolet radiation, this method has the advantage of a great degree of freedom in the selection of the type of light with respect to wavelength of the illuminating light, type of light source device, and the like. Moreover, if visible light is selected as the illuminating light, imaging and illumination may be performed, for example, using illumination for imaging (flash lighting) of a normal camera, camera-equipped cellular phone, camera-equipped multifunctional portable phone (smart phone), or the like. Based on the presence or absence of reflected light in the obtained image, it is possible to determine the presence or absence of the marker composition.

Applications of the marker composition of the present embodiment are exemplified by indicators used for determination of degree of cleanliness when cleaning in facilities such as hospitals, hotels, restaurants, and the like. In particular, in hospitals there is danger of cross infection from one patient to another within the hospital due to the hospital being visited by patients infected with various types of diseases. Thus in addition to sufficiently cleaning the interior of the hospital, it is important to determine with good accuracy whether the cleaning inside the hospital has been sufficiently performed. The marker composition of the present embodiment in such an application is extremely useful due to the ability to sense the degree of cleanliness with good accuracy by a simple method that detects the presence or absence of the marker composition in a wide range.

Second Embodiment: Marker Composition

The marker composition of the second embodiment contains retroreflective particles and a dispersion medium soluble in water.

The same particles as the retroreflective particles of the first embodiment can be used as the retroreflective particles of the second embodiment. Here, duplicate explanations will be omitted.

From the perspectives of applicability, visibility, and reflectivity, the content ratio of the retroreflective particles in the marker composition of the second embodiment is preferably from 60 to 80 mass %, more preferably from 70 to 80 mass %, and even more preferably from 75 to 80 mass % on the basis of the entire mass of the marker composition. In addition, when the content ratio of the retroreflective particles is within the range described above, the marker composition can be wiped away more easily, and the marker composition can be used over a wider temperature range.

No particular limitation is placed on the dispersion medium, and the dispersion medium may be any water-soluble dispersion medium. The dispersion medium may be wax-like or paste-like at room temperature (25° C.). Here, the term "wax-like" means solid-like or wax-like at room temperature. Moreover, the term "paste-like" means that the dispersion medium is in a state (i.e. Bingham fluid state) in which flow does not occur at room temperature unless a certain external force is applied (i.e. yield stress).

The pour point of the dispersion medium is preferably 0 to 60° C., further preferably is 10 to 55° C., and most preferably is 20 to 40° C. By setting the pour point in the aforementioned range, it is possible to improve viscosity, adhesion ability, and application property of the marker composition. Here, the term "pour point" means the pour point as measured based on JIS K 2269.

The weight-basis ratio of retroreflective particles to dispersion medium may be set to 90:10 to 50:50, or 85:15 to 55:45, or 80:20 to 60:40.

The dispersion medium preferably includes a nonionic surfactant. By this means, the marker composition may be more readily wiped off using a wetted cloth or the like. No particular limitation is placed on the nonionic surfactant as long as the nonionic surfactant is gel-like or paste-like. Polyethylene glycol type nonionic surfactants and polyhydric alcohol type nonionic surfactants, for example, may be used as this type of nonionic surfactant. Furthermore, if the dispersion medium does not include a softening agent, the pour point of the nonionic surfactant is preferably 0 to 60° C., further preferably is 10 to 55° C., and most preferably is 20 to 40° C.

Moreover, the dispersion medium may include a nonionic surfactant and a softening agent. By use of such a composition, viscosity, adhesion ability, and application property of the marker composition may be improved. In this case, it is possible to more readily adjust the pour point of the dispersion medium by setting the type and content of the softening agent appropriately according to the type and content of the nonionic surfactant. Thus there is an increased degree of freedom of choice of the type and content of the nonionic surfactant used in the dispersion medium. For example, by addition of a softening agent to a nonionic surfactant having a pour point in excess of 60° C., it is possible to make the pour point of the overall dispersion medium in a range that is preferably 0 to 60° C., further preferably is 10 to 55° C., and most preferably is 20 to 40° C. Moreover, in the present aspect, a nonionic surfactant may be used that has a pour point that is preferably 0 to 60° C., further preferably is 10 to 55° C., and most preferably is 20 to 40° C.

The nonionic surfactant is exemplified by polyoxyethylene, polyol, siloxane, polyoxyethylene oleyl ether, polyoxyethylene lauryl ether, polyoxyethylene isocetyl ether, and polyoxyethylene polyoxypropylene block copolymer (under trade names such as Pluronic, Tween, Poloxamer, and Span). Such nonionic surfactants may be used as one type or as a combination of two or more types.

The content of the nonionic surfactant in the total dispersion medium is preferably 30 to 100% by weight, further preferably is 45 to 100% by weight, and most preferably is 60 to 100% by weight.

No particular limitation is placed on the softening agent, as long as the softening agent softens the dispersion medium. Softening agents that may be used are exemplified by water-soluble substances that are liquids at 4 to 60° C.

Softening agents are exemplified by glycerin, polyethylene glycol, polypropylene glycol, sorbitan sesquioleate, sorbitan sesqui-isostearate, sorbitan oleate, sorbitan isostearate, palm oil fatty acid sorbitan, Polysorbate 80, lauryl alcohol, oleyl alcohol, phenol ethoxylate, polyethylene glycol oleate, polyoxyalkylene ether tallowate, caprylyl glycol, diglycerin lauryl ester, diglycerin oleyl ester, hexaglycerin caproate, decaglycerin lauryl ester, and the like.

The content of the softening agent in the total dispersion medium is preferably 3 to 50% by weight, further preferably is 20 to 40% by weight, and most preferably is 25 to 35% by weight.

The marker composition of the present embodiment may be utilized in a state that includes substantially no water except for naturally absorbed moisture. The moisture content due to naturally absorbed moisture is preferably less than or equal to 10% by weight, further preferably is less than or equal to 5% by weight, and most preferably is less than or equal to 3% by weight.

The marker composition of this embodiment may further contain other additives (plasticizers, moisturizers, surfactants, preservatives, or the like) within a scope that does not diminish the essence of the present invention.

The marker composition of the present embodiment may be obtained by blending of the retroreflective particles, the water-soluble dispersion medium, and as may be required, additives such as the softening agent or the like. No particular limitation is placed on the order of blending of these components, and for example, all the components may be fed to into a vessel and then blended, or alternatively, after blending of part of the components, the other components may be added and blended in the mixture. The preferred method of preparation is exemplified by a method composed of a step of obtaining the dispersion medium by firstly blending the components included in the dispersion medium, and then a step of obtaining the marker composition by adding and blending the retroreflective particles in the dispersion medium. The processing conditions of each of these steps may be selected appropriately. Moreover, the softening agent or the like additives may be added at the time of preparation of the dispersion medium, or alternatively, these additives may be added together with the retroreflective particles to the dispersion medium, or these additives may be added to the dispersion medium after addition of the retroreflective particles.

Third Embodiment: Applicator

The applicator of the third embodiment is provided with the marker composition and an applicator capable of retaining the marker composition. The marker composition may be readily applied by this means. Here, "retention" includes housing or storing the marker composition inside the applicator body. In addition, the marker composition of the first embodiment or the second embodiment may be used as the marker composition in this embodiment.

The aforementioned applicator body may be porous. By this means, the retention ability of the marker composition by the applicator body becomes good, and it is possible to further improve the ability to apply the marker composition.

The aforementioned applicator body may have interconnected cells within the applicator body. The marker composition within the applicator body may be readily transferred by this means, and thus the marker composition becomes retained in a more uniform manner by the applicator body. It is thus possible for this applicator to more uniformly apply the marker composition.

The cell count of the aforementioned interconnected cells is preferably 15 to 100 per 25 mm, further preferably is 25 to 70 per 25 mm, and most preferably is 35 to 45 per 25 mm. As a result, the transferability (ease of filling the applicator body with the marker composition, ease of applying the marker composition, or the like) of the marker composition and the retention ability of the marker composition in the applicator body can be improved with good balance. Thus the applicator of this aspect is capable of application of the marker composition with greater uniformity even when the applicator is repeatedly used. In the present specification, the term "cell count" indicates the number of cells per 25 mm.

The aforementioned applicator may be further composed of a retention body for retaining the aforementioned applicator body so that at least part of the aforementioned applicator body is exposed, and a lid body, detachably attached to the aforementioned retention body, for hermetic sealing of the exposed part of the aforementioned applicator body. Long-term storage of the marker composition becomes possible by this means.

FIG. 1 is a perspective view illustrating another example of the applicator of the present embodiment. The applicator 30 is composed of an applicator body 32 capable of retaining the marker composition, a retention body 34 for retaining the applicator body 32, a lid body 36 (detachably attached to the retention body 34) for hermetically sealing the applicator body 32, and a sealing component 38 (mounted on the retention body 34) for sealing the gap between the retention body 34 and the lid body 36. The applicator body 32 is constructed from a porous material, and the marker composition is retained within the applicator body 32. That is, in the applicator 30 illustrated in FIG. 1, the applicator body 32 provides a function as a retention body for housing or storing the marker composition in addition to the original function as the applicator body of the marker composition.

A porous substance (e.g. sponge) may be used as the applicator body 32. The applicator body 32 preferably has interconnected cells within the interior of the applicator body 32, and the cell count of such interconnected cells is preferably 30 to 100 per 25 mm.

No particular limitation is placed on the substances of the retention body 34 and the lid body 36, and this substance may be metal, plastic, glass, or the like. Moreover, the retention body 34 and lid body 36 may be transparent or colored.

An O-ring may be used as the sealing component 38, for example. No particular limitation is placed on the substance of the sealing component 38, and this substance may be rubber or the like. Moreover, the sealing component 38 may be transparent or colored.

A male thread part 34*a* is arranged at the applicator body 32 side of the side part exterior wall face of the retention body 34, and a female thread part 36 is arranged in the region of the opening side of the inner wall face of the lid body 36. According to this aspect, the hermetic sealing of the applicator body 32 and the attachment of the lid body 36 to the retention body 34 are possible by screwing together of the male thread part 34*a* and the female thread part 36*a*, and storage stability of the marker composition may be increased. Moreover, the retention body 34 is shaped such that, when the retention body 34 is sliced by a vertical plane along the A axis in FIG. 1, cross-sectional area of the part where the male thread part 34*a* is arranged becomes smaller than the cross-sectional area of the part where the male thread part 34*a* is not arranged. The sealing component 38 has a ring shape, and the outer wall face of the inside of the sealing component 38 is capable of fitting the outside wall face of the part of the retention body 34 where the male thread part 34*a* is arranged. The sealing component 38 is mounted by fitting the side part outer wall face of the part of the retention body 34 where the male thread part 34*a* is arranged, so as to contact the interface between the part of the retention body 34 where the male thread part 34*a* is arranged and the part where the male thread part 34*a* is not arranged. When the lid body 36 is mounted on the retention body 34, the sealing component 38 is sandwiched between the lid body 36 and the aforementioned interface of the retention body 34, and the gap between the retention body 34 and the lid body 36 is sealed. It is thus possible to increase air tightness of the space for hermetic sealing of the applicator body 32. Thus according to this aspect, degradation, evaporation, or the like of the marker composition can be effectively suppressed, and it is possible to further increase storage stability of the marker composition. Moreover, by carrying the applicator about in this condition, the marker composition becomes readily transported, and it is possible to prevent leakage of the marker composition from the applicator body 32 and to prevent adhesion of the marker composition to the skin, clothing, or the like.

Moreover, during application of the marker composition, by unscrewing apart of the male thread part 34*a* and the female thread part 36*a*, the lid body 36 becomes separated from the retention body 34, and it is possible to open the applicator body 32.

Moreover, the means for attaching the lid body to the retention body of the applicator illustrated in FIG. 1, may use any shape capable of joining together the retention body and the lid body, such as a shape in which the outer wall face of the retention body and the inner wall face of the lid body each have roughly the same cross-sectional shape (when viewed in cross-section cut vertically along the A axis in FIG. 1), or the like. Moreover, a protruding part capable of fitting the inner wall face of the lid body may also be arranged in the outer wall face of the retention body, or the like, to form a shape capable of latching the lid body to the retention body. By using the sealing component to seal the gap between the retention body and the lid body also for these attachment means, it is possible to further increase air tightness of the space for hermetic sealing of the applicator body.

When the applicator 30 is used for applying the marker composition, for example, the side part of the retention body 34 is grasped, and the exposed part of the applicator body 32 is pressed against the surface of the application target, or alternatively, the applicator 30 is rotated while in contact with the application target, so that the marker composition may be adhered or transferred to the surface of the application target. This type of application uses the applicator 30 as a stamp-type applicator. According to this method, in the surface of the application target, a single or multiple application regions may be formed corresponding to the shape of the part of the applicator target contacting the surface of the applicator body 32.

Moreover, the exposed part of the applicator body 32 may perform application of the marker composition by being moved along the surface of the application target while being pressed against the surface of the application target. According to this method, it is possible to form a strip-shaped application region on the face of the application target, and it is possible to use the marker composition to fully coat a certain region on the face of the application target.

Shape and size of the applicator 30 may be selected appropriately in consideration of ready portability, ease of grasping during application, ease of attachment of the lid body 36 to the retention body 34, ease of detachment of the lid body 36 from the retention body 34, and the like. For example, total length of the applicator 30 along the A axis in FIG. 1 may be set to 10 to 50 mm, and the diameter of the cross-section obtained by slicing the applicator 30 along a perpendicular plane at the A axis in FIG. 1 may be set to 5 to 30 mm.

The method for production of the applicator 30 is composed of a step of using the marker composition to fill the applicator body 32, a step of attaching the applicator body 32 filled by the marker composition to the retention body 34, and a step of attaching the lid body 36 to the retention body 34, for example.

Moreover, the method of using the marker composition to fill the applicator body 32 may feed the marker composition to the applicator body 32 through a fill nozzle connected to a pump, for example. The processing conditions of this method (e.g. marker composition feed rate, marker composition pressure, processing temperature, or the like) may be selected appropriately according to physical properties of the marker composition (e.g. viscosity, fluid flow properties, or the like), physical properties of the applicator body 32 (e.g. size and cell count of the interconnected cells, or the like), or the like. During filling, as may be required, heated marker composition may be fed to the applicator body 32. Moreover, if the marker composition is fed to the applicator body 32 while the applicator body 32 is shaken, it is possible to readily fill the applicator body 32 with the marker composition and to spread the marker composition in the interior part of the applicator body 32. Furthermore, the surface of the applicator body 32 filled by the marker composition may undergo grinding processing.

The applicator of the present embodiment is not limited to the aforementioned aspect, and various modifications are possible. For example, in the applicator illustrated in FIG. 1, the means for hermetically sealing the applicator body may have a shape capable of joining together the retention body and lid body, for example, have a shape for the retention body and lid body in which a retention body outer wall face and lid body inner wall face each have roughly the same cross-sectional shape when sliced vertically at the A axis in FIG. 1. Moreover, the applicator may have a screw-type fastener to make possible detachable attachment of the lid body to the retention body. Furthermore, by use of a sealing component to seal the gap between the retention body and the lid body, it is possible to increase air tightness of the space for hermetic sealing of the applicator body. Moreover, due to greatly increased storage stability of the marker composition during storage of the applicator, storage is permissible by inserting the applicator in a highly hermetically sealed container (e.g. bag, housing, or the like).

When the applicator body of the applicator does not have a function as a retainer for housing or storing the marker composition on the inside, the marker composition can be applied by supplying the marker composition to the applicator body from the vessel (reservoir) housing or storing the marker composition. However, when the marker composition is applied to a plurality of hospital rooms in a hospital using such an applicator, for example, it is necessary to be sufficiently cautious so that there is no contamination of the marker composition inside the applicator body or the reservoir at the time of use or no spread of pathogens due to the use of the contaminated applicator at other locations. In addition, when the reservoir is damaged as a result of the applicator being accidentally dropped on the floor, for example, the contaminated marker composition may scatter and cause pathogens to be diffused over a wide area, so sufficient caution is required when handling the applicator. For this issue, when the applicator illustrated in FIG. 1 is used, a plurality of applicators should be prepared in advance, and the applicator body of an applicator used in a given hospital room should be hermetically sealed with a lid after use or should be stored in the hospital room or discarded after use, so as to use other applicators for applying the marker composition in other hospital rooms. This leads the advantage of preventing the spread of pathogens due to contaminated applicators. Further, in the applicator illustrated in FIG. 4, the marker composition is retained inside the applicator body. Therefore, even if the applicator is accidentally dropped on the floor or the like, it is unlikely that the marker composition will scatter, which is useful from the perspective of preventing the spread of pathogens.

Fourth Embodiment: Applicator Set

The applicator set of the fourth embodiment includes a plurality of applicators each including the marker composition and an applicator body capable of retaining the marker composition. Each of the applicators has a retention body for retaining the applicator body. The retention body includes a retention part retaining the applicator body so that at least part of the applicator body is exposed, and a lid part capable of detachably attaching to the retention parts of other applicators, and capable of hermetically sealing the exposed part of the applicator body of other applicators. The marker composition of the first embodiment or the second embodiment may be used as the marker composition in this embodiment.

One of the applicators among the aforementioned multiple applicators may be capable of being distinguished from the other applicators. In this case, it is possible to readily determine whether all the applicators provided by the applicator set have been used (i.e. determination of the time to end use of the applicator set). Moreover, each of the multiple applicators may be capable of being distinguished from the other applicators. In this case, it becomes easy to use different applicators of the multiple applicators according to differing locations, usages, or the like. Although no particular limitation is placed on the means for distinguishing between the applicators, such means are exemplified by use of a color, material, shape (e.g. concavity), or the like on at least part of the applicator so as to differ from the other applicators, and the application of markers to the applicators.

Figure 2:
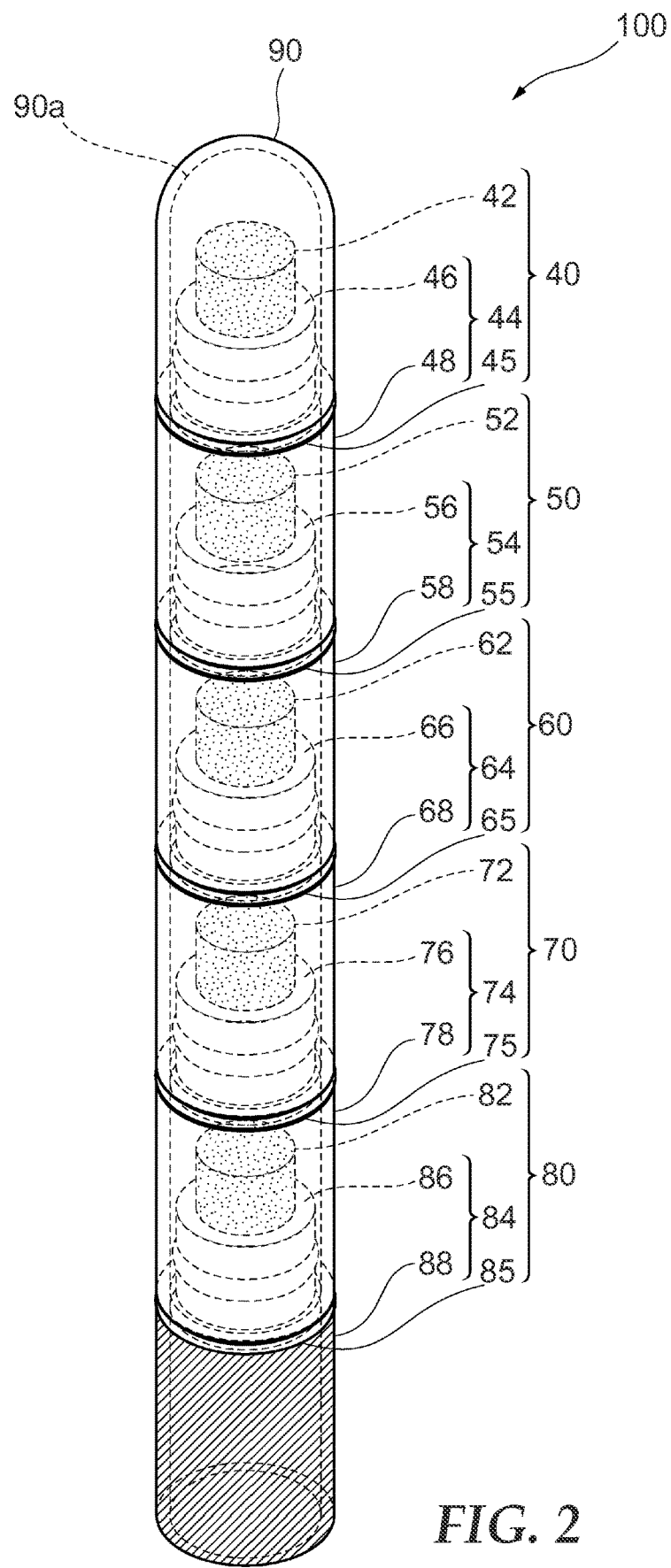
FIG. 2 is a perspective view illustrating an example of the applicator set of the fourth embodiment.
Figure 3:
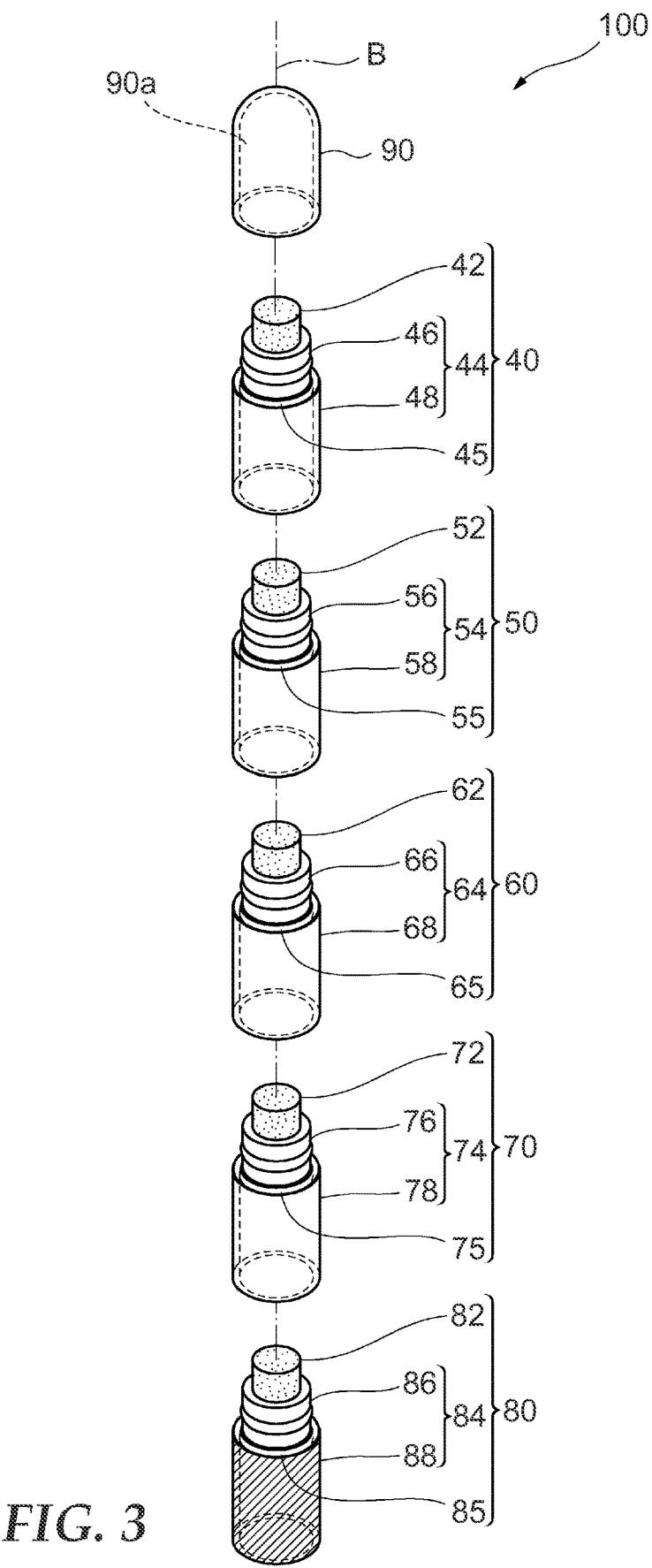
FIG. 3 is an exploded view of the applicator set illustrated in FIG. 2.

FIG. 2 is a perspective view illustrating an example of the applicator set of the present embodiment. Moreover, FIG. 3 is an exploded view of the applicator set illustrated in FIG. 2. The applicator set 100 is composed of applicators 40, 50, 60, 70, and 80, and lid body 90. Hereafter, the applicators 40 and 50 and the lid body 90 will be used as examples to explain the relationships of adjacent elements in detail, but the configurations and shapes of the applicators 40, 50, 60, 70, and 80 (configurations and shapes of the other means, when the means capable of distinguishing as described above is applied) may be the same as one another.

The applicator 40 is composed of an applicator body 42, a retention body 44 for retention of the applicator body 42, and a sealing component 45 attached to the retention body 44 for sealing the gap between the retention body 44 and the lid body 90. A retention part 46 at the side near the applicator body 42, and a lid part 48 at the side far from the applicator body 42, are arranged in the retention body 44. The retention part 46 has a shape such that cross-sectional area of the tip part distant from the applicator body 42 becomes larger than cross-sectional area of the tip part near the applicator body 42 when the retention body 44 is sliced at a certain position along a vertical plane at the B axis in the FIG. 3, and the retention part 46 has a shape so as to fit and to well hermetically seal the opening part of the lid body 90. The sealing component 45 has a ring shape, and the exterior wall face of the interior of the sealing component 45 is capable of fitting the side part exterior wall face of the retention part 46. The sealing component 45 is made capable of contacting the interface between the retention part 46 and the lid part 48, and it is attached by fitting together with the side part exterior wall face of the retention part 46. When the lid body 90 is fit onto the retention part 46, the sealing component 45 is sandwiched between the lid body 90 and the aforementioned interface surface of the retention body 44, and the gap between the retention body 44 and the lid body 90 is sealed so that it is possible to increase air tightness of the space for hermetically sealing the applicator body 42. Moreover, the opening part of the lid part 48 has a shape capable of fitting well and hermetically sealing with the adjacent applicator 50 and the retention part 56 thereof. When the lid part 48 fits together with the retention part 56, the sealing component 55 of the applicator 50 seals the gap between the retention body 54 and the lid part 58, so that air tightness of the space for hermetic sealing of the applicator body 52 may be increased.

By this means, the applicator 40 and the lid body 90 may be connected in a detachably attached manner with good hermetic sealing, the applicator 40 and the applicator 50 may be connected in a detachably attached manner with good hermetic sealing, and it is possible to increase storage stability of the marker composition. Moreover, by carrying about the applicator in this state, the marker composition may be readily transported, it is possible to prevent leakage of the marker composition from the applicator bodies 42 and 52, and it is possible to prevent adhesion of the marker composition to the skin, clothing, or the like.

Moreover, by separation of the applicator 40 from the lid body 90 during application of the marker composition, it is possible to open the applicator body 42, and it is possible to apply the marker composition retained in the applicator body 42.

For example, by grasping the side part of the applicator set 100 in the state in which the applicators 40, 50, 60, 70, and 80 are joined together, simply by pressing the exposed part of the applicator body 42 of the applicator 40 at the distal tip position against the surface of the application target, it is possible to adhere or transfer the marker composition to the surface of the application target. This application method uses the applicator set 100 as a stamp type applicator, and according to this method, it is possible to form one or multiple application regions corresponding to the shape of the part of the applicator body 42 contacting the surface of the application target.

Moreover, the marker composition may be applied by movement of the exposed part of the applicator body 42 along the surface of the application target in a state in which the exposed part is pressed against the application target. According to this method, it is possible to form a strip-shaped application region on the face of the application target, and it is possible to use the marker composition to fully coat a certain region on the face of the application target.

Furthermore, after application of the marker composition, the spent applicator 40 may be separated from the adjacent applicator 50, and the spent applicator 40 may be joined to the applicator 80 positioned at the other tip of the applicator set 100, so as to open the applicator body 52 at the applicator 50. By then pressing the exposed part of the applicator body 52 against the surface of the application target, it is possible to apply the marker composition retained by the applicator body 52. This method uses the applicator set 100 as a multi-stamp type applicator. For example, during use within the medical ward of a hospital, even if a pathogen adheres to the applicator body 42 of the applicator 40, the applicator body 42 is hermetically sealed by the lid part 88 of the applicator 80, and it is thus possible to prevent the spread of the pathogen to other hospital wards. In addition, the spread of pathogens due to a contaminated applicator can also be prevented by storing or discarding the applicator 40 used in a given hospital room in the room after use and applying the marker composition in other hospital rooms using the applicator set 100 from which the applicator 40 has been separated.

Shape and size of the applicator set 100 may be selected appropriately in consideration of factors such as ease of transport, ease of grasping during application, ease of attachment-detachment of the applicators 40, 50, 60, 70, and 80 and the lid body 90, or the like. For example, diameter of the cross section obtained by cutting the applicator set 100 along a vertical plane including the B axis in FIG. 3 may be set to 5 to 20 mm, and the overall length of the applicator set along the B axis in FIG. 3 may be set to 10 to 50 mm.

Moreover, no particular limitation is placed on the material of the retention body 44, 54, 64, 74, 84, and the lid body 90, and this material may be a metal, plastic, glass, or the like. Moreover, the retention body 44, 54, 64, 74, 84, and the lid body 90 may be transparent or colored.

An O-ring may be used as the sealing component 45, 55, 65, 75, and 85, for example. No particular limitation is placed on the substance of the sealing components 45, 55, 65, 75, and 85, and this substance may be transparent or colored.

The method of production of the applicator set 100 is exemplified by a method composed of: a step of using the marker composition to fill each of the applicator bodies 42, 52, 62, 72, and 82; a step of attaching the applicator bodies 42, 52, 62, 72, and 82 filled by the marker composition to the retention bodies 44, 54, 64, 74, and 84, respectively, to obtain the applicators 40, 50, 60, 70, and 80, respectively; and a step of joining together the applicators 40, 50, 60, 70, and 80, and the lid body 90.

Moreover, the method of using the marker composition to fill the applicator bodies 42, 52, 62, 72, and 82 is exemplified by the method of feeding the marker composition to the applicator bodies 42, 52, 62, 72, and 82 through a fill nozzle connected to a pump. The processing conditions of this method (e.g. marker composition feed rate, marker composition pressure, processing temperature, or the like) may be selected appropriately according to physical properties of the marker composition (e.g. viscosity, fluid flow properties, or the like), physical properties of the applicator body 32 (e.g. size and cell count of the interconnected cells, or the like), or the like. During filling, as may be required, heated marker composition may be fed to the applicator bodies 42, 52, 62, 72, and 82. Moreover, if the marker composition is fed to the applicator bodies 42, 52, 62, 72, and 82 while the applicator bodies 42, 52, 62, 72, and 82 are shaken, it is possible to readily fill the applicator bodies 42, 52, 62, 72, and 82 with the marker composition and to spread the marker composition in the interior part of the applicator bodies 42, 52, 62, 72, and 82. Furthermore, the surface of the applicator bodies 42, 52, 62, 72, and 82 filled by the marker composition may undergo grinding processing.

The applicator set of the present embodiment is not limited to the aforementioned aspect, and various types of variations are possible. For example, the means of connection between separate applicators and the means of connection between the applicator and the lid body, in the same manner as the applicator of the third embodiment, may arrange a male thread part at the retention part of the applicator, arrange a female thread part at the lid body and lid part of the applicator, and may perform attachment by screwing together these threaded members. Moreover, the lid part may be shaped so as to be capable of latching with the retention part, for example, by providing the exterior wall face of the retention part with a protuberance part capable of latching with the inner wall face of the lid part. It is possible by such joining means to use the sealing component to seal the gap between the retention part and the lid part and to increase air tightness of the space for hermetically sealing the applicator body. Moreover, the applicator and lid body may each have a fastener to make the applicator and lid body capable of mutual detachable attachment. Furthermore, the applicator set may be inserted and stored in a highly hermetically sealed container (e.g. bag, housing, or the like) in order to further increase storage stability of the marker composition during storage of the applicator set.

In addition, no particular limitation is placed on the number of applicators of the applicator set, and a single applicator set may have from 1 to 20 applicators.

Fifth Embodiment: Applicator Set

The applicator set of the fifth embodiment is provided with the marker composition and a plurality of applicators having applicator bodies capable of retaining the marker composition. Each applicator is further equipped with a retention body for retaining the applicator body so that at least part of the applicator body is exposed, and a lid body which is detachably attached to the retention body so as to hermetically seal the exposed portion of the applicator body. In addition, the applicator set described above is further equipped with a fixing member for integrally fixing a plurality of applicators. The marker composition of the first embodiment or the second embodiment may be used as the marker composition in this embodiment.

One of the applicators among the aforementioned multiple applicators may be capable of being distinguished from the other applicators. In this case, it is possible to readily determine whether all the applicators provided by the applicator set have been used (i.e. determination of the time to end use of the applicator set). Moreover, each of the multiple applicators may be capable of being distinguished from the other applicators. In this case, it becomes easy to use different applicators of the multiple applicators according to differing locations, usages, or the like. Here, although no particular limitation is placed on the means for distinguishing between the applicators, such means are exemplified by use of a color, material, shape (e.g. concavity), or the like on at least part of the applicator so as to differ from the other applicators, by the application of markers to the applicators, and by the application of markers to the fixing member.

Figure 4:
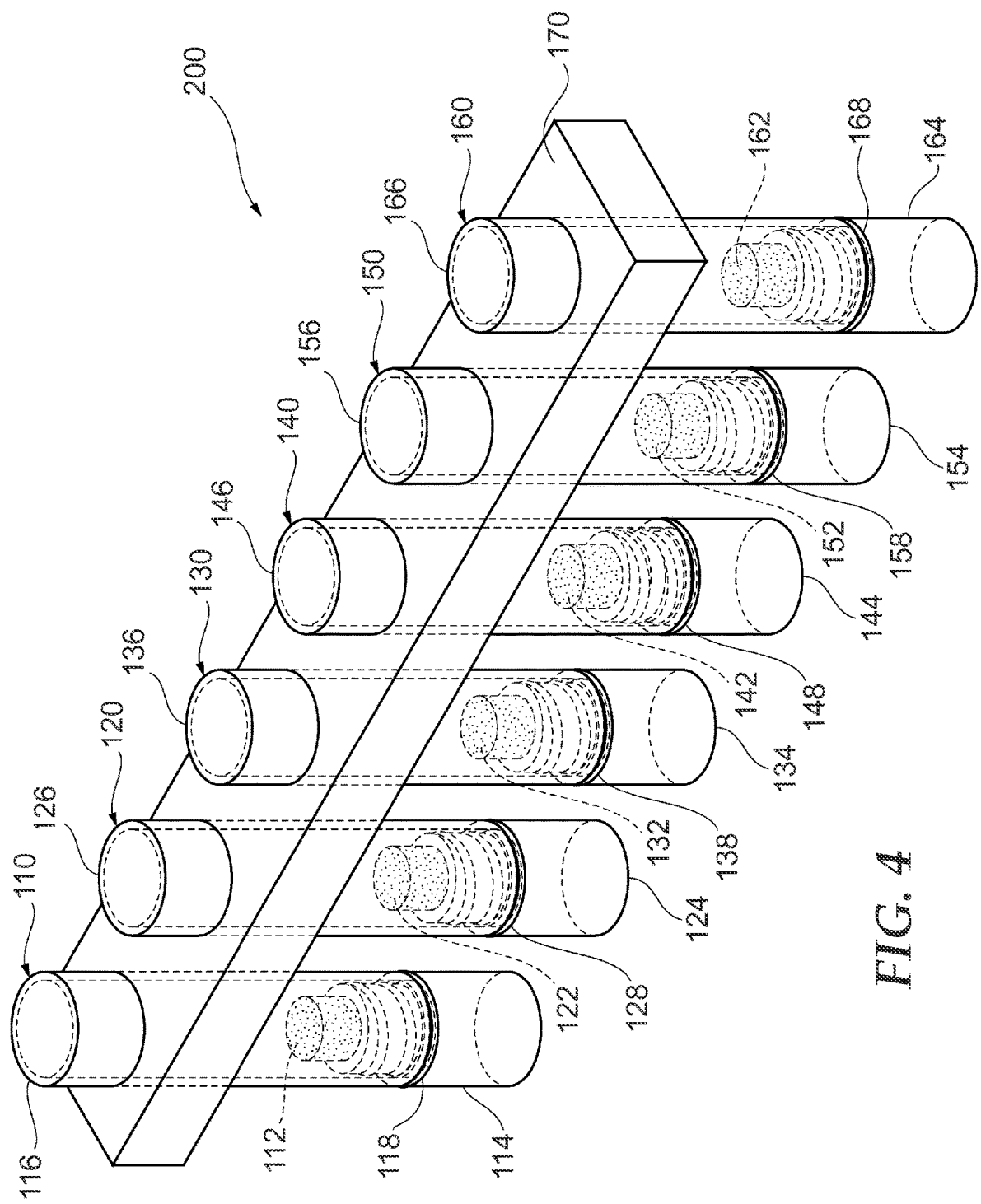
FIG. 4 is a perspective view illustrating an example of the applicator set of the fifth embodiment.

FIG. 4 is a perspective view illustrating an example of the applicator set of the present embodiment. The applicator set 200 is equipped with applicators 110, 120, 130, 140, 150, and 160 and a fixing member 170. Hereafter, the relationship between the applicator 110 and the fixing member 170 will be explained as an example, but the relationships between the applicators 120, 130, 140, 150, and 160 and the fixing member 170 are also the same as the relationship between the applicator 110 and the fixing member 170. In addition, the configurations and shapes of the applicators 110, 120, 130, 140, 150, and 160 (when a means capable of distinguishing between applicators as described above is applied, these are the configurations and shapes of parts other than this means) may be the same as one another. For example, the respective applicators 110, 120, 130, 140, 150, and 160 may have the same configurations and shapes as the applicators illustrated in FIG. 1.

The applicator 110 is composed of an applicator body 112 capable of retaining the marker composition, a retention body 114 for retaining the applicator body 112, a lid body 116 (detachably attached to the retention body 114) for hermetically sealing the applicator body 112, and a sealing component 38 (mounted on the retention body 114) for sealing the gap between the retention body 114 and the lid body 116. The fixing member 170 has a roughly rectangular parallelepiped shape and is provided with a plurality of through-holes at prescribed spacings toward the longitudinal direction. The through-holes pass through from the central part in the width direction of one side surface of the fixing member 170 toward the central part in the width direction of the side surface of the opposite side. The respective through-holes pass through the fixing member 170 in parallel to one another. The through-holes can engage with the outer peripheral surface of the lid body 116. The applicator 110 is detachably attached to the fixing member 170 as a result of the lid body 116 engaging with one of the through-holes.

The material of the fixing member 170 is not particularly limited and may be metal, plastic, glass, or the like. In addition, the fixing member 170 may be transparent or colored.

The shape and size of the fixing member 170 may be selected appropriately in consideration of factors such as the ease of transport, ease of fixing the applicators 110 and 120 to the fixing member 170, and ease of attaching and detaching the applicators 110, 120, 130, 140, 150, and 160 to and from the fixing member 170. For example, the total length of the fixing member 170 along the longitudinal direction of the fixing member 170 in FIG. 4 may be set to 50 to 300 mm.

With such an applicator set 200, it is possible to integrally fix the applicators 110, 120, 130, 140, 150, and 160 to the fixing member 170. In addition, by carrying around the applicator set 200, the transportation of a plurality of applicators becomes easy.

By separating the lid body 116 from the applicator 110, for example, at the time of the application of the marker composition, it is possible to separate the applicator 110 from the applicator set 200 and to open the applicator body 112. By then gripping the applicator 110 separated from the lid body 116 and pressing the exposed portion of the applicator body 112 against the surface of the application target, it is possible to apply the marker composition retained in the applicator body 112. When the lid body 116 and the fixing member 170 are detachably attached, the lid body 116 may be separated from the applicator 110 so as to apply the marker composition after the applicator 110 is separated from the fixing member 170 in a state in which the lid body 116 is mounted.

After the application of the marker composition, the applicator body 112 of the used applicator 110 is hermetically sealed by the lid body 116. Next, by separating the lid body 126 from the applicator 120, for example, it is possible to separate the applicator 120 from the applicator set 200 and to open the applicator body 122. By then gripping the applicator 120 separated from the lid body 126 and pressing the exposed portion of the applicator body 122 against the surface of the application target, it is possible to apply the marker composition retained in the applicator body 122. For example, even if a pathogen becomes attached to the applicator body 112 of the applicator 110 during use within the hospital room of a hospital, the applicator body 112 is hermetically sealed by the lid part 116, so it is possible to prevent the spread of the pathogen to other hospital wards. In addition, the spread of pathogens due to a contaminated applicator can also be prevented by storing or discarding the applicator 110 used in a given hospital room in the room after use and applying the marker composition in other hospital rooms using the applicator set 200 from which the applicator 110 has been separated.

An example of a method of production of the applicator set 200 is a method comprising: a step of filling the applicator bodies 112, 122, 132, 142, 152, and 162 with the marker composition; a step of mounting the respective applicator bodies 112, 122, 132, 142, 152, and 162 filled with the marker composition to the retention bodies 114, 124, 134, 144, 154, and 164 to obtain the applicators 110, 120, 130, 140, 150, and 160; and a step of fixing the applicators 110, 120, 130, 140, 150, and 160 to the fixing member 170.

The applicator set of the present embodiment is not limited to the aforementioned aspect, and various types of variations are possible. For example, the means of connection between separate applicators and the means of connection between the applicator and the lid body, in the same manner as the applicator of the third embodiment, may arrange a male thread part at the retention part of the applicator, arrange a female thread part at the lid body and lid part of the applicator, and may perform attachment by screwing together these threaded members. Moreover, the lid part may be shaped so as to be capable of latching with the retention part, for example, by providing the exterior wall face of the retention part with a protuberance part capable of latching with the inner wall face of the lid part. It is possible by such joining means to use the sealing component to seal the gap between the retention part and the lid part and to increase air tightness of the space for hermetically sealing the applicator body. Moreover, the applicator and lid body may each have a fastener to make the applicator and lid body capable of mutual detachable attachment. Furthermore, the applicator set may be inserted and stored in a highly hermetically sealed container (e.g. bag, housing, or the like) in order to further increase storage stability of the marker composition during storage of the applicator set.

In addition, the fixing member is not particularly limited as long as it integrally fixes a plurality of applicators. For example, an adhesive for detachably adhering the applicators to one another may be used as the fixing member.

In addition, no particular limitation is placed on the number of applicators of the applicator set, and a single applicator set may have from 1 to 20 applicators.

Sixth Embodiment: Method of Determining Degree of Cleanliness

The method of determining the degree of cleanliness of the sixth embodiment comprises: a step of applying the marker composition to the pre-cleaning surface to be cleaned; a step of radiating light on the post-cleaning surface to be cleaned, and sensing light reflected from retroreflective particles; and a step of determining the degree of cleanliness of the surface to be cleaned based on the results of sensing the reflected light. The marker composition of the first embodiment or the second embodiment may be used as the marker composition in this embodiment. In addition, the method of applying the marker composition is not particularly limited, and it is possible, for example, to use the applicator of the third embodiment, the applicator set of the fourth embodiment, or the applicator set of the fifth embodiment.

In one aspect of the degree of cleanliness determination method of the present embodiment, firstly, the marker composition is applied to an object to be cleaned (e.g. table, chair, or the like) or to the floor, wall, ceiling, or the like prior to cleaning, in a manner so as not to be noticed by the cleaning personnel. Furthermore, if the region of application of the marker composition is not to be known by the cleaning personnel, a transparent composition may be used for the marker composition.

Thereafter, the cleaning personnel perform cleaning. The marker composition may be readily removed from the cleaning region by wiping off using a cleaning tool (e.g. cloth, mop, or the like) that includes water, a mixed solution of water-alcohol, or the like. Furthermore, during application and removal of the marker composition, the marker composition is illuminated by light as natural lighting or indoor lighting. However, since the line of sight of the person holding the cleaning article and cleaning the cleaning region is normally different from the direction of incidence and reflection of light, the person holding the cleaning article and cleaning the cleaning region is normally unable to visually sense reflected light from the retroreflective particles.

Thereafter, light is irradiated onto the post-cleaning surface to be cleaned, light reflected form the retroreflective particles is sensed, and then based on the results of sensing of the reflected light, the degree of cleanliness of the surface to be cleaned is determined No particular limitation is placed on the illuminating light as long as the illuminating light indicates retroreflectivity of the retroreflective particles. Moreover, if the utilized light is visible light, it is possible to visually sense the reflected light. Alternatively, illumination and imaging may be performed using light emission for imaging (flash lighting) of a normal camera, camera-equipped cellular phone, camera-equipped multi-function type portable phone, or the like; and then based on the presence or absence of reflected light in the obtained image, it is possible to determine the presence or absence of the marker composition.

Seventh Embodiment: System for Determining Degree of Cleanliness

The system for determining the degree of cleanliness of the seventh embodiment comprises: a sensing means, upon application of the marker composition and thereafter radiation of light onto the post-cleaning surface to cleaned, for sensing reflected light from retroreflective particles based on image data showing condition of the surface to be cleaned after the cleaning; and a determination means for determining the degree of cleanliness of the surface to be cleaned based on results of sensing the reflected light obtained by the sensing means.

No particular limitation is placed on the image data of the present embodiment, as long as the image data are capable of use in determining the presence or absence of light reflected from the retroreflective particles included in the marker composition means by the sensing means. For example, in the same manner as in the seventh embodiment, light illumination for imaging (flash lighting) of a normal camera, a camera-equipped cellular phone, a camera-equipped multifunctional phone, or the like may be used.

No particular limitation is placed on the sensing means, as long as the sensing means is capable of sensing light reflected from the retroreflective particles included in the marker composition based on the obtained image data. For example, it is possible to use an image analysis device capable of distinguishing the presence or absence of reflected light in the image data. Moreover, during sensing of the reflected light, as may be required, it is possible to perform image processing such as increasing the contrast between the region of reflected light in the image data (bright region) and other regions (dark regions). Processing may also be performed such as the analysis of the surface area and/or shape of the region where there is reflected light. It is possible to determine the degree of cleanliness of the surface to be cleaned with higher accuracy by performing such analysis.

No particular limitation is placed on the determination means, as long as the determination means is able to determine the degree of cleanliness of the surface to be cleaned based on the results of sensing of reflected light obtained by the sensing means. For example, if the sensing means has a function for transmission of a data signal relating to the result of sensing the reflected light, it is possible to use a data processing device having the ability to receive the data signal and having a function for determination that "reflected light is present" or "reflected light is absent" based on the information signal.

Furthermore, by use of a means for exchanging information (e.g. intranet, internet, or the like), uniform management of data is possible relating to the results of determination of the degree of cleanliness based on image data or the results of sensing of reflected light obtained at multiple locations. By this means, efficient and accurate determination of whether or not cleaning has been sufficiently performed may be carried out even when the region subject to cleaning extends over a wide range.

A multifunction type device having both a sensing function and determination function may be used for the sensing means and determination means. A camera-equipped multifunction type portable phone may be used as this type of multifunction type device, for example. In this case, firstly, software (i.e. an application) for executing a function for the aforementioned sensing means and determination means is installed in a computer (CPU or the like) within the portable phone. Thereafter, by processing of the image data by the aforementioned software, it is possible to sense light reflected form the retroreflective particles and the perform a determination of the degree of cleanliness of the surface to be cleaned. Software to realize the function of the sensing means and software to realize the function of the determination means may be separate software applications, or may be a single integrated software application.

Moreover, a means for data exchange may be used, and a server computer capable of being accessed (i.e. a so-called cloud system) may be used as the multifunction type device. In this case, firstly software for realizing the functions of the sensing means and determination means is installed in the server computer. Thereafter, the data exchange means is used to send the image data to the server computer. Thereafter, the server computer uses the aforementioned software to perform processing of the image data, and then the processing results are received from the server computer so that, at the cleaning site, it is possible to readily perform sensing of light reflected from the retroreflective particles and determination of the degree of cleanliness of the surface to be cleaned, even when there is no sensing means and determination means at the cleaning site.

EXAMPLES

Although the present invention is explained more concretely based on working examples, the present invention in no manner is limited by the below working examples.

Production Examples 1 and 2

<Preparation of Mixture of Dispersion Medium and Humectant>

The respective water soluble polymers, water, alcohols, and humectants indicated below were used in the Production Examples 1 and 2 to prepare the mixtures of dispersion medium and humectant having the compositions indicated in Table 1. Furthermore, the units of the blended fractions of each of the materials in Table 1 are parts by weight.
Water-Soluble Polymer:
X-PVP (produced by Aldrich, water soluble polymer obtained by γ radiation of polyvinylpyrrolidone to crosslink)
K90-PVP (produced by Wako Pure Chemical Industries, Ltd., non-crosslinked polyvinylpyrrolidone)
Water: deionized water
Alcohol: IPA (isopropyl alcohol)
Humectant: glycerin The method of preparation of the mixtures of dispersion medium and humectant in the Productions Examples 1 and 2 were as follows.

Firstly, at a temperature of 4 to 6° C., the deionized water and glycerin were placed in a hermetically sealed vessel used for blending of flammable solvents, and the water soluble polymer was added, and mixing was continued. Thereafter, temperature of the mixture was raised to 25° C., and then IPA was added to this mixture, and the mixture was blended to obtain the mixture of the dispersion medium and humectant.

<Measurement of Viscosity of the Dispersion Medium and Humectant>

Viscosity (cps) at 25° C. of the mixture of dispersion medium and humectant of the Production Examples 1 and 2 was measured based on JIS Z 8803. The measurement results are shown in Table 1.

TABLE 1

|  |  | Production example | |
|---|---|---|---|
| Material |  | 1 | 2 |
| Water-soluble polymer | X-PVP | 10 | — |
|  | K90-PVP | — | 10 |
| Water | Deionized water | 35 | 35 |
| Alcohol | IPA | 50 | 50 |
| Moisturizing agent | glycerin | 5 | 5 |
| Viscosity (cps, 25° C.) |  | 29300 | 8250 |

Working Examples 1 Through 4

<Preparation of the Marker Composition>

In Working Examples 1 to 4, the marker compositions having the compositions respectively indicated in Table 2 were prepared using retroreflective particles, a water soluble polymer, water, an alcohol, and a humectant. Furthermore, the units of each of the blended fractions of each of the materials in Table 2 are parts by weight. Moreover, details of the materials indicated in Table 2 are described below.
Retroreflective Particles:
UB-24M (produced by Unitika Ltd., glass particles having 45 to 63 μm particle diameter and 1.9 refractive index)
UB-35M (produced by Unitika Ltd., glass particles having 53 to 75 μm particle diameter and 1.9 refractive index)
Water-Soluble Polymer:
X-PVP (produced by Aldrich, water soluble polymer obtained by γ radiation of polyvinylpyrrolidone to crosslink)
K90-PVP (produced by Wako Pure Chemical Industries, Ltd., non-crosslinked polyvinylpyrrolidone)
K30-PVP (produced by Wako Pure Chemical Industries, Ltd., non-crosslinked polyvinylpyrrolidone)
Water: deionized water
Alcohol: IPA (isopropyl alcohol)
Humectant: glycerin The methods of preparation of the marker composition in Working Examples 1 to 4 are described below.

Firstly, at a temperature of 4 to 6° C., the deionized water and glycerin were placed in a hermetically sealed vessel used for blending of flammable solvents, and the mixture was mixed. Then, the water-soluble water is added and mixed. Thereafter, temperature of the mixture was raised to 25° C., and then IPA was added to this mixture, and the mixture was blended. Then the retroreflective particles were further added, and the mixture was blended to obtain the marker composition.

<Preparation of the Applicator, and Evaluation of Characteristics of the Marker Composition>

Using each of the marker compositions of the Working Examples 1 to 4, respective applicators were produced. The applicator production procedure is described below.

Firstly, a polyurethane sponge (produced by INOAC Corp., trade name: CFH-40, interconnected cell count: 40 per 25 mm) was prepared as the applicator body. Next, while stirring the marker composition at 70° C., the marker composition was fed to the sponge from a pump connected to a peristaltic pump, and the marker composition soaked into the sponge. The amount of marker composition per polyurethane sponge was set at 0.5 to 0.6 g. At this time, the ease of filling the sponge with the marker composition and the retention ability of the marker composition were evaluated. The evaluation criteria are described below.

(Ease of Filling the Sponge)
  A: The sponge is very easy to fill.
  B: The sponge is easy to fill.
  C: The sponge is somewhat difficult to fill.

(Sponge Retention Ability)
When the sponge was filled with the marker composition, it was evaluated whether the marker composition is retained well in the sponge on the basis of the following criteria.
  A: The marker composition is retained very well.
  B: The marker composition is retained well.
  C: The marker composition is somewhat difficult to retain.

Thereafter, the sponge was mounted on the retention body, and the lid body and sealing component (O-ring) were mounted on the retention body to obtain a stamp type applicator as shown in FIG. 1.

Thereafter, the lid body was removed from the applicator to uncover the sponge, and the marker composition was applied by pressing the exposed part of the sponge against a piece of paper. The piece of paper to which the marker composition was applied was then observed visually, and the application ability of the marker composition (ease of attachment and thickness of the applied marker composition) was evaluated. Moreover, the piece of paper after application of the marker composition was evaluated by using a camera to image the state when not illuminated by imaging light and to image the state when illuminated by imaging light, and visibility (visibility of the marker composition when not illuminated by light) and reflectivity (ease of seeing the marker composition when illuminated by light) were evaluated based on the obtained images.

The evaluation criteria for each characteristic were as follows.

(Application Property)
  A: The marker composition is applied very well.
  B: The marker composition is applied well.
  C: The marker composition is somewhat difficult to attach.
  D: The marker composition is thickly applied.

(Visibility)
  A: The marker composition is very difficult to see.
  B: The marker composition is difficult to see.
  C: The marker composition is easy to see.

(Reflectivity)
  A: The marker composition is very easy to see.
  B: The marker composition is easy to see.
  C: The marker composition is difficult to see.

Further, the ease of wiping off the marker composition from a piece of paper and the stability of the marker composition retained in the sponge of the applicator were evaluated.

(Ease of Wiping Off)
  A: The marker composition is very easy to wipe off.
  B: The marker composition is easy to wipe off.
  C: The marker composition is somewhat difficult to wipe off.

(Stability)
The below listed criteria were used for evaluation of whether the marker composition was stably retained by the sponge without excessively leaking from the sponge retaining the marker composition.
  A: The marker composition is retained very stably.
  B: The marker composition is retained stably.
  C: The marker composition is somewhat difficult to retain stably.

Figure 5:
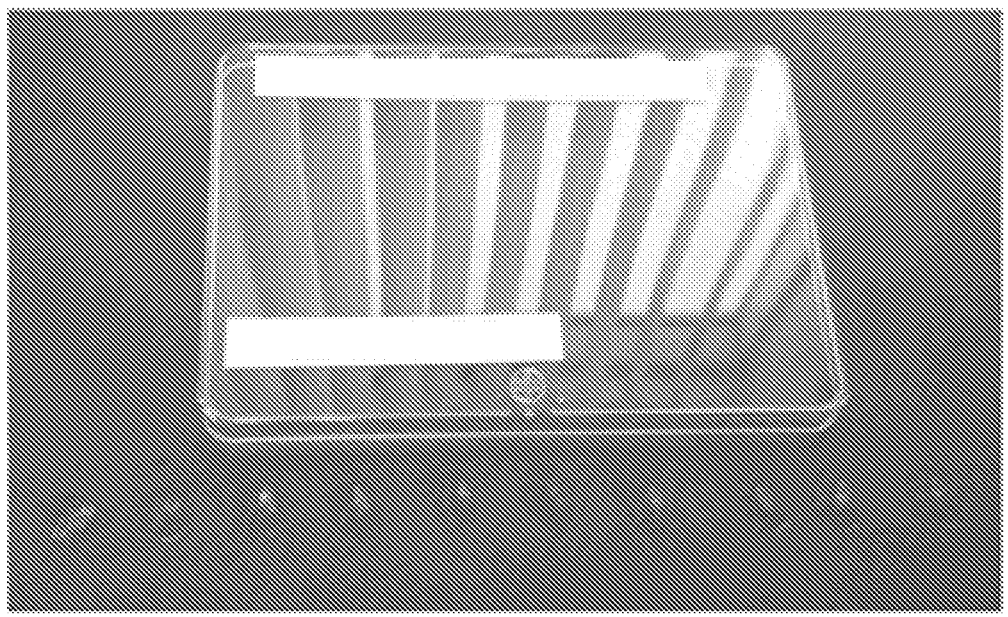
FIG. 5 is an image illustrating the piece of paper to which the marker composition of Working Example 1 has been applied, in a state without irradiation of imaging light.
Figure 6:
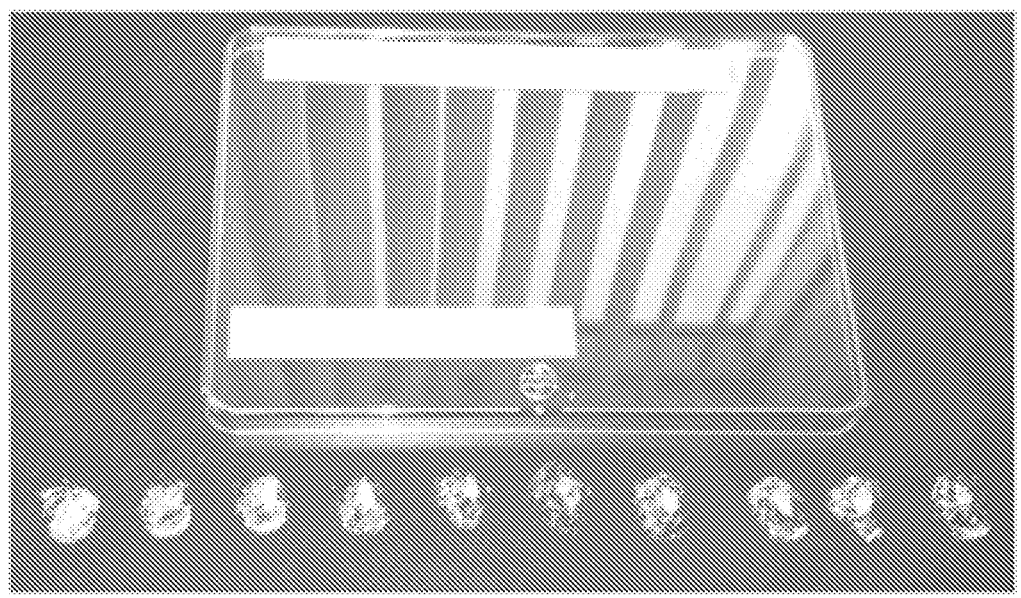
FIG. 6 is an image illustrating the piece of paper to which the marker composition of Working Example 1 has been applied, in a state with irradiation of imaging light.

The obtained results of evaluation are shown in Table 2. FIG. 5 illustrates an image of the state of the piece of paper to which the marker composition of Working Example 1 was applied, when not illuminated by imaging light. FIG. 6 illustrates an image of the state of the piece of paper to which the marker composition of Working Example 1 was applied, when illuminated by imaging light. The multiple transfers of the marker composition in FIGS. 5 and 6 were made using the same applicator. Regarding visibility and reflectivity, there is essentially no difference between the evaluation results obtained when the applied marker composition was observed with the naked eye and the evaluation results based on photographs. For example, when it is not possible to visually confirm the marker composition in a photograph illustrating a state without radiation of imaging light, it is also not possible to visually confirm the marker composition with the naked eye.

TABLE 2

| | | Embodiment | | | |
|---|---|---|---|---|---|
| Material | | 1 | 2 | 3 | 4 |
| particles | UB-24M | — | — | 80.0 | — |
| | UB-35M | 80.0 | 80.0 | — | 80.0 |
| Water-soluble polymer | X-PVP | — | — | — | 1.50 |
| | K-90PVP | 2.00 | 1.50 | — | — |
| | K-30PVP | — | — | 2.00 | — |
| Water | Deionized water | 7.00 | 10.25 | 7.00 | 10.25 |
| Alcohol | IPA | 10.00 | 7.50 | 10.00 | 7.50 |
| Moisturizing agent | glycerin | 1.00 | 0.75 | 1.00 | 0.75 |
| Rating | Ease of filling | B | C | B | A |
| | retention ability | A | A | A | A |
| | application property | A | A | C | C |
| | visibility | A | A | A | A |
| | reflectivity | A | A | B | B |
| | ease of wiping off | A | A | A | A |
| | stability | A | A | A | A |

Production Examples 3 to 5

Marker compositions were made using the blend concentrations of each of the ingredients and the combination of ingredients, water soluble polymer, water, alcohol, humectant, and pH adjustment agent as shown in Table 3. Furthermore, the units of blend fraction for each of the materials in Table 3 was parts by weight. "PVA #1400" in Table 3 is polyvinylalcohol (produced by Kishida Chemical Co., Ltd., trade name: Polyvinylalcohol 1,400).

TABLE 3

| | | Production example | | |
|---|---|---|---|---|
| Material | | 3 | 4 | 5 |
| Water-soluble polymer | Hydroxyethyl-cellulose | 5 | — | — |
| | Hydroxypropyl methyl cellulose phthalate | — | 5 | — |
| | PVA#1400 | — | — | 5 |
| Water | Deionized water | 67.5 | 40.0 | 67.5 |
| Alcohol | IPA | 25 | 50 | 25 |
| Moisturizing agent | glycerin | 2.5 | — | 2.5 |
| pH adjusting agent | 0.6M NaOH | — | 5.0 | — |

Working Examples 5 Through 7

<Preparation of the Marker Composition>

Marker compositions having the respective compositions shown in Table 4 were prepared in Working Examples 5 to 7. Furthermore, the preparation procedure of the marker composition was the same as in Working Examples 1 to 4. Moreover, the units of blend fractions of each of the materials in Table 4 are parts by weight.

<Preparation of the Applicator, and Evaluation of Characteristics of the Marker Composition>

Using each of the marker compositions of the Working Examples 5 to 7, respective applicators were produced. The preparation procedure of the applicator was the same as in Working Examples 1 to 4. Using the obtained applicator, the marker composition was applied to a piece of paper at a temperature of 4° C., 25° C., or 40° C., and the reflectivity of the marker composition was evaluated in accordance with the same evaluation criteria as in Working Examples 1 to 4.

Further, the attachment ability of the marker composition (strength of the adhesion to the piece of paper) and the ease of wiping away from the piece of paper were evaluated based on the following evaluation criteria.

(Attachment Ability)

A: The marker composition is attached well.

B: The marker composition is somewhat difficult to attach.

C: The marker composition is very strongly attached.

(Ease of Wiping Off)

A: The marker composition is very easy to wipe off.

B: The marker composition extends and expands but is easy to wipe off.

C: The marker composition is somewhat difficult to wipe off.

Figure 7:
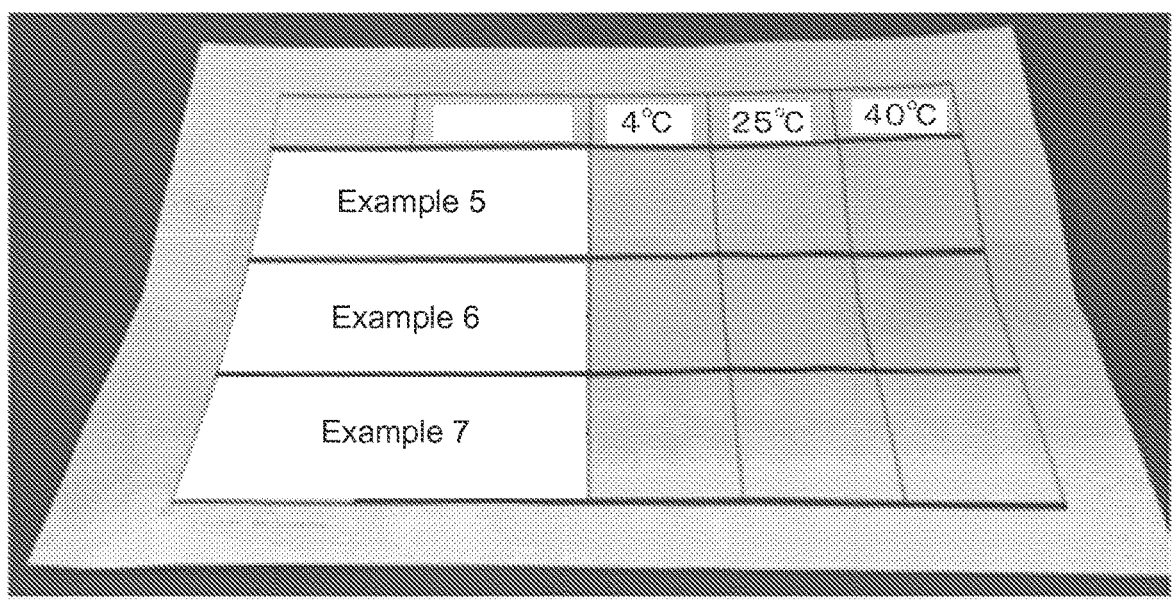
FIG. 7 is an image illustrating the piece of paper to which the marker compositions of Working Examples 5 to 7 have been applied, in a state without irradiation of imaging light.
Figure 8:
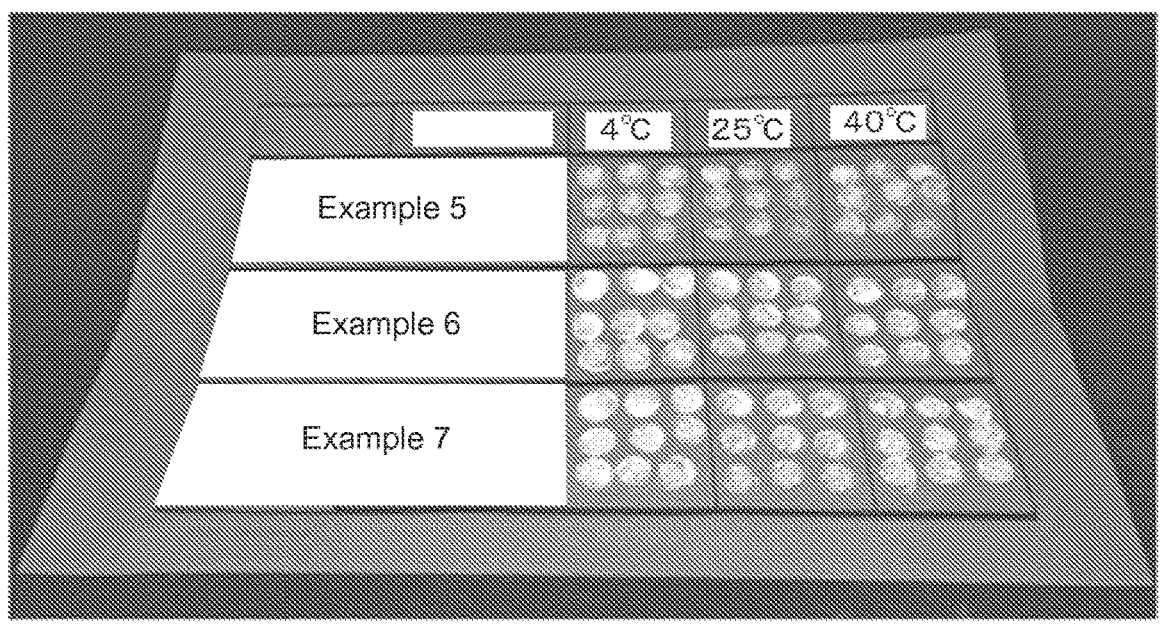
FIG. 8 is an image illustrating the piece of paper to which the marker compositions of Working Examples 5 to 7 have been applied, in a state with irradiation of imaging light.

The obtained results of evaluation are shown in Table 4. Moreover, FIG. 7 shows an image of the state of the piece of paper to which the marker compositions of Working Examples 5 to 7 were applied, when not illuminated by imaging light. FIG. 8 shows an image of the state of the piece of paper to which the marker compositions of Working Examples 5 to 7 were applied, when illuminated by imaging light. The multiple transfers of the marker compositions in FIGS. 7 and 8 at each temperature in Working Examples 5 to 7 were made using the same respective applicator. Regarding visibility and reflectivity, there is essentially no difference between the evaluation results obtained when the applied marker composition was observed with the naked eye and the evaluation results based on photographs.

TABLE 4

| | | | Embodiment | | |
|---|---|---|---|---|---|
| | Material | | 5 | 6 | 7 |
| particles | UB-35M | | 80.0 | 80.0 | 80.0 |
| Water-soluble polymer | K-90PVP | | 2.0 | 1.0 | 0.6 |
| Water | Deionized water | | 17.0 | 17.0 | 15.4 |
| Moisturizing agent | glycerin | | 1.0 | 2.0 | 4.0 |
| Rating | state of the composition (25° C.) | | Solid | Solid | Rice cake-like |
| | Attachment ability | | C | A | B |
| | reflectivity | 4° C. | A | A | A |
| | | 25° C. | A | A | A |
| | | 40° C. | A | A | A |
| | ease of wiping off | 4° C. | C | A | B |
| | | 25° C. | C | A | B |
| | | 40° C. | C | A | B |

Working Examples 8 & 9

<Preparation of the Marker Composition>

In Working Examples 8 and 9, the retroreflective particles and dispersion medium indicated below were used, and the marker compositions having the compositions indicated in Table 5 were prepared. Furthermore, the units of the blended fractions of each of the materials in Table 5 are parts by weight.

Retroreflective Particles:

UB-24M (produced by Unitika Ltd., glass particles having 45 to 63 μm particle diameter and 1.9 refractive index)

Dispersion Medium:

Pluronic (registered trade name) 25R4 (produced by BASF, pour point: 25° C.) Poloxamer 188 (produced by Merck & Co., Inc., pour point: 52° C.)

The marker compositions of Working Examples 8 and 9 were prepared by placing the retroreflective particles and dispersion medium in a planetary mixer at 90° C. and blending the mixture. Then the obtained marker composition was maintained at a temperature of 70° C. to 90° C., and the marker composition was used for production of the below described applicator set.

<Production of Applicator Set, and Evaluation of Marker Composition>

An applicator was produced using a respective marker composition of Working Examples 8 and 9. The applicator production procedure is described below.

Firstly, a polyurethane sponge (produced by INOAC Corp., trade name: MF-50, cell count: 50 per 25 mm) was prepared as the applicator body. Next, while stirring the marker composition at 70° C., the marker composition was fed to the sponge from a pump connected to a peristaltic pump, and the marker composition soaked into the sponge. The amount of marker composition per polyurethane sponge was set at 0.5 to 0.8 g. At this time, the retention ability of the marker composition by the sponge was evaluated.

Thereafter, the sponges were mounted on the retention bodies to obtain the applicators, and the multiple applicators and lid bodies were mutually connected together to obtain a multi-stamp type applicator set such as that illustrated in FIG. 2.

Thereafter, the lid body was separated from the applicator disposed at the distal tip to expose the sponge, and application of the marker composition was performed by pressing the exposed part of the sponge against a piece of paper. Further, a series of steps comprising separating the used applicator from the tip of the applicator set, mounting the applicator to the end of the applicator set, and applying the marker composition was repeated, and the application ability of the marker composition (uniformity of the thickness of the applied marker composition), the ease of exchanging applicators, and the recoatability when applied with a new applicator were evaluated. Moreover, the piece of paper after application of the marker composition was evaluated by using a camera to image the state when not illuminated by imaging light and to image the state when illuminated by imaging light, and visibility (visibility of the marker composition when not illuminated by light) and reflectivity (ease of seeing the marker composition when illuminated by light) were evaluated based on the obtained images.

Further, the ease of wiping off the marker composition from a piece of paper and the stability of the marker composition retained in the sponge of the applicator were evaluated.

The evaluation criteria are described below.
(Sponge Retention Ability)

When the sponge was filled with the marker composition, it was evaluated whether the marker composition is retained well in the sponge on the basis of the following criteria.
A: The marker composition is retained very well.
B: The marker composition is retained well.
C: The marker composition is somewhat difficult to retain.
(Application Property)
A: The marker composition is applied very uniformly.
B: The marker composition is applied uniformly.
C: The marker composition is somewhat difficult to apply uniformly.
(Visibility)
A: The marker composition is very difficult to see.
B: The marker composition is difficult to see.
C: The marker composition is easy to see.
(Reflectivity)
A: The marker composition is very easy to see.
B: The marker composition is easy to see.
C: The marker composition is difficult to see.
(Ease of Wiping Off)
A: The marker composition is very easy to wipe off.
B: The marker composition is easy to wipe off.
C: The marker composition is somewhat difficult to wipe off.
(Stability)

The below listed criteria were used for evaluation of whether the marker composition was stably retained by the sponge without excessively leaking from the sponge retaining the marker composition.
A: The marker composition is retained very stably.
B: The marker composition is retained stably.
C: The marker composition is somewhat difficult to retain stably.
(Ease of Replacement of Applicator)
A: The applicator is very easy to replace.
B: The applicator is easy to replace.
C: The applicator is difficult to replace.
(Recoating Ability)
A: Very easy to recover.
B: Easy to recoat.
C: Difficult to recoat.

Figure 9:
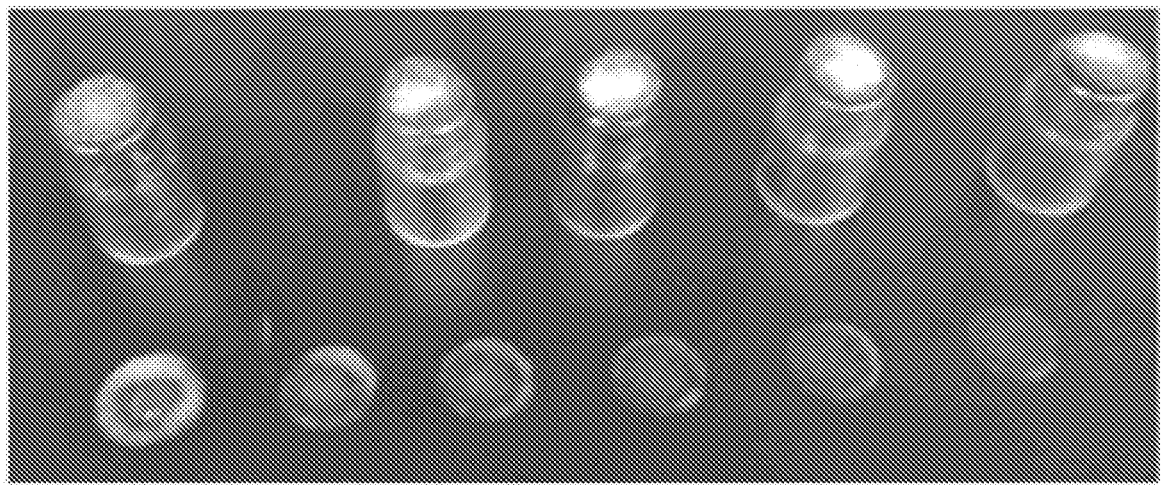
FIG. 9 is an image illustrating the applicator produced using the marker composition of Working Example 8 and the piece of paper to which the marker composition of Working Example 8 has been applied, in a state without irradiation of imaging light.
Figure 10:
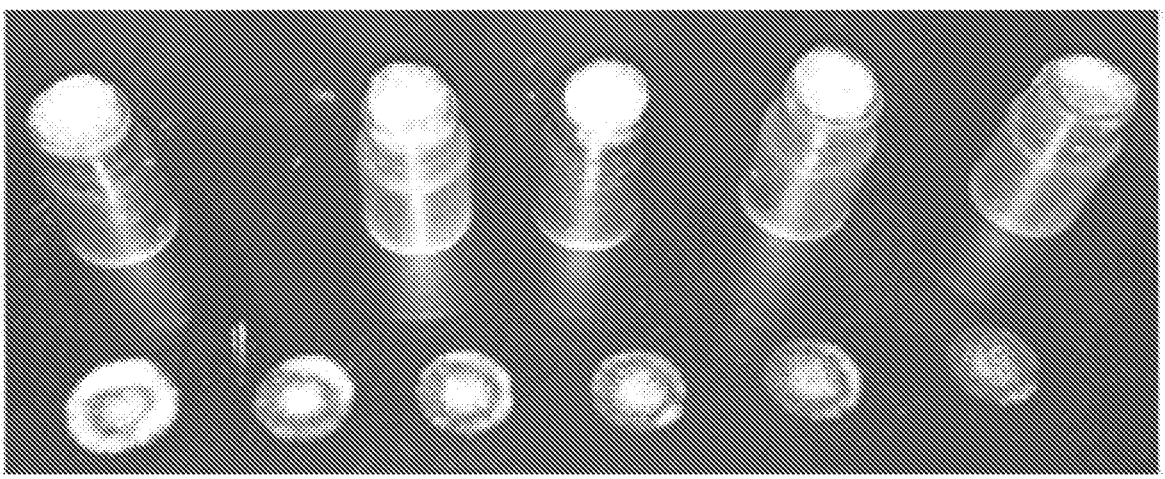
FIG. 10 is an image illustrating the applicator produced using the marker composition of Working Example 8 and the piece of paper to which the marker composition of Working Example 8 has been applied, in a state with irradiation of imaging light.
Figure 11:
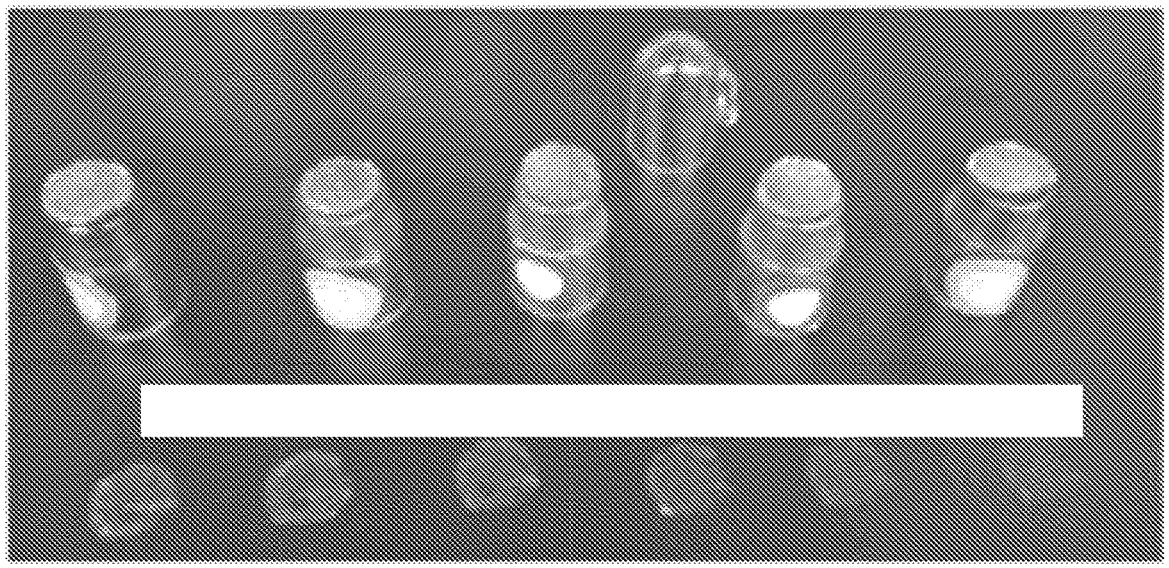
FIG. 11 is an image illustrating the applicator produced using the marker composition of Working Example 9 and the piece of paper to which the marker composition of Working Example 9 has been applied, in a state without irradiation of imaging light.
Figure 12:
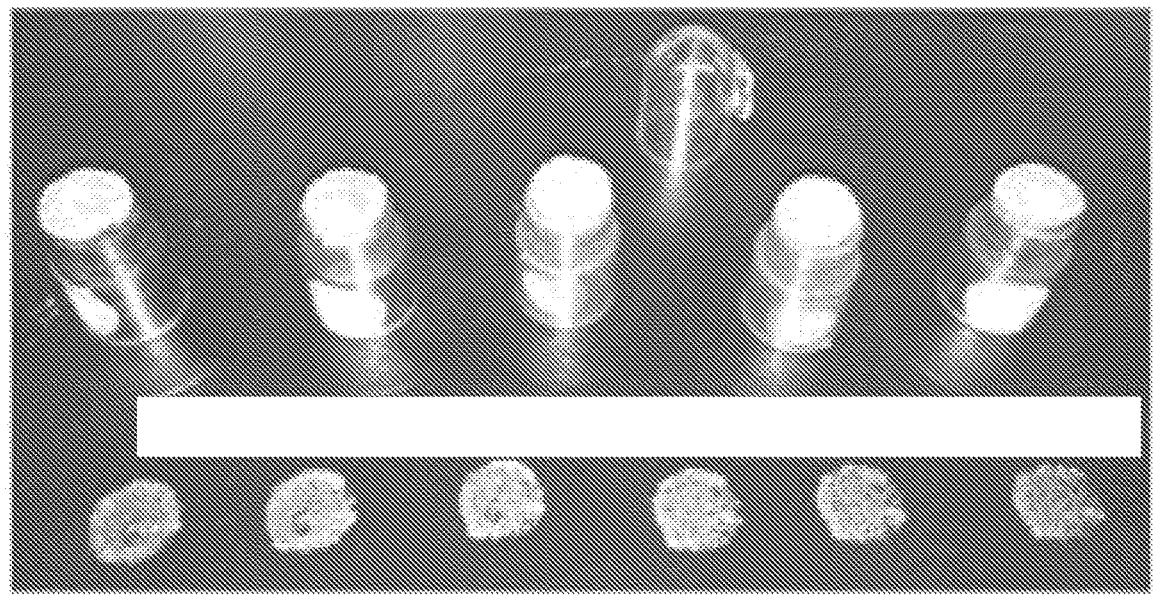
FIG. 12 is an image illustrating the applicator produced using the marker composition of Working Example 9 and the piece of paper to which the marker composition of Working Example 9 has been applied, in a state with irradiation of imaging light.

The obtained results of evaluations are shown in Table 5. Moreover, for the applicator produced using the marker composition of Working Example 8 and the piece of paper coated using the marker composition of Working Example 8, an image illustrating the state when not illuminated by imaging light is illustrated in FIG. 9, and an image illustrating the state when illuminated by imaging light is illustrated in FIG. 10. Moreover, for the applicator produced using the marker composition of Working Example 9 and the piece of paper coated using the marker composition of Working Example 9, an image illustrating the state when not illuminated by imaging light is illustrated in FIG. 11, and an image illustrating the state when illuminated by imaging light is illustrated in FIG. 12. Each of the multiple transfers of the marker composition in FIGS. 9 to 12 were made using the same respective applicator. Regarding visibility and reflectivity, there is essentially no difference between the evaluation results obtained when the applied marker composition was observed with the naked eye and the evaluation results based on photographs.

TABLE 5

|  |  | Embodiment | |
| --- | --- | --- | --- |
| | Material | 8 | 9 |
| particles | UB-24M | 70 | 70 |
| a dispersion medium; | Pluronic 25R4 | 30 | — |
| | Poloxamer 188 | — | 30 |
| Rating | state of the composition (25° C.) | paste | wax |
| | retention ability | A | A |
| | application property | A | A |
| | visibility | B | A |
| | reflectivity | A | A |
| | ease of wiping off | A | A |
| | stability | C | A |
| | ease of replacement | A | A |
| | recoating ability | A | A |

<Production of Applicator Set, and Evaluation of Marker Composition Characteristics>

Figure 13:
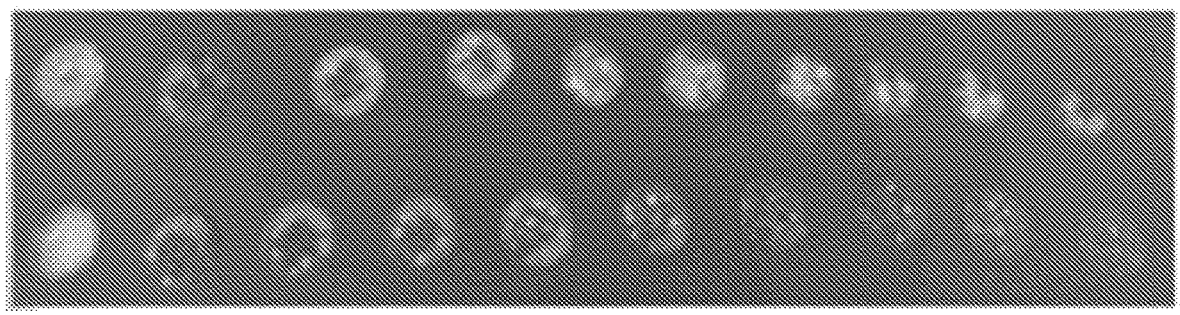
FIG. 13 is an image illustrating the piece of paper to which the marker composition of Working Example 8 has been applied, in a state without irradiation of imaging light.
Figure 14:
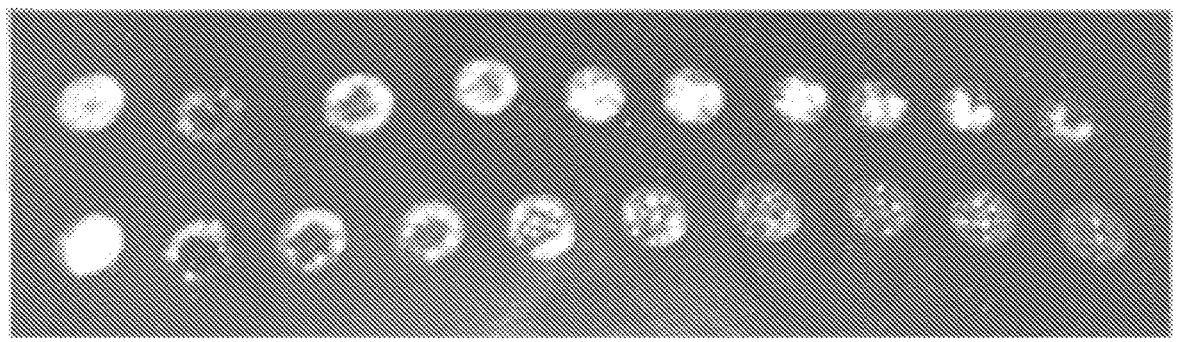
FIG. 14 is an image illustrating the piece of paper to which the marker composition of Working Example 8 has been applied, in a state with irradiation of imaging light.

Applicator sets were obtained using the marker composition of Working Example 8 and in the same manner as in Working Example 8, except for change of the sponge (urethane foam) used for stamping to the sponge indicated in Table 6. Furthermore, details of the materials indicated in Table 6 are listed below.
MF-20: Produced by INOAC Corp., Polyester Type Urethane Foam, Trade Name, Cell Count: 20 Per 25 mm
MF-30: produced by INOAC Corp., polyester type urethane foam, trade name, cell count: 30 per 25 mm
CFH-30: produced by INOAC Corp., polyester type urethane foam, trade name, cell count: 30 per 25 mm
CFH-40: produced by INOAC Corp., polyester type urethane foam, trade name, cell count: 40 per 25 mm
MF-50: produced by INOAC Corp., polyester type urethane foam, trade name, cell count: 50 per 25 mm
MF-55: produced by INOAC Corp., polyester type urethane foam, trade name, cell count: 55 per 25 mm Next, the applicators of the obtained applicator sets were used, the marker composition of Working Example 8 was applied 10 times to a piece of paper, and retention ability and application property were evaluated. The obtained results are shown in Table 6. In addition, when an applicator having CFH-30 or CFH-40 as a sponge was used, an image of the state of a piece of paper to which the marker composition of Working Example 8 was applied, without radiation of imaging light, is shown in FIG. 13, and an image of the state of a piece of paper to which the marker composition of Working Example 8 was applied, with radiation of imaging light, is shown in FIG. 14. Here, in FIGS. 13 and 14, the upper level indicates the results for CFH-30, and the lower level indicates the results for CFH-40. Each of the multiple transfers of the marker composition in FIGS. 13 and 14 was made using the same respective applicator.

TABLE 6

| Material sponge | | MF-20 | MF-30 | CFH-30 | Working Example 8 CFH-40 | MF-50 | MF-55 |
|---|---|---|---|---|---|---|---|
| cell count (no. per 25 mm) | | 20 | 30 | 30 | 40 | 50 | 55 |
| Rating | retention ability | A | A | A | A | B | C |
|  | application property | C | B | B | A | A | A |

Working Examples 10 Through 13

<Preparation of the Marker Composition>
Marker compositions having the respective compositions shown in Table 7 were prepared in Working Examples 10 to 13. Furthermore, details of the materials indicated in Table 7 are listed below. Moreover, the units of blend fractions of each of the materials in Table 7 are parts by weight.
Pluronic 25R4: produced by BASF, trade name, pour point: 25° C.
Pluronic P84: produced by BASF, trade name, pour point: 34° C.
Pluronic P103: produced by BASF, trade name, pour point: 30° C.
Poloxamer 188: produced by Merck & Co., Inc., trade name, pour point: 52° C.
<Production of Applicator Set, and Evaluation of Marker Composition Characteristics>
Respective applicator sets were produced using the marker compositions of Working Examples 10 to 13. Except for use of MF-55 as the sponge, the production procedure of the applicator sets was the same as that of Working Examples 8 and 9. Thereafter, the obtained applicator sets were used to apply the marker compositions of Working Examples 10 to 13 to pieces of paper. The retention ability, application ability, visibility, reflectivity, ease of wiping off, stability, ease of replacement, and recoatability of the marker compositions were then evaluated in accordance with the same evaluation criteria as in Working Examples 8 and 9.

Figure 15:
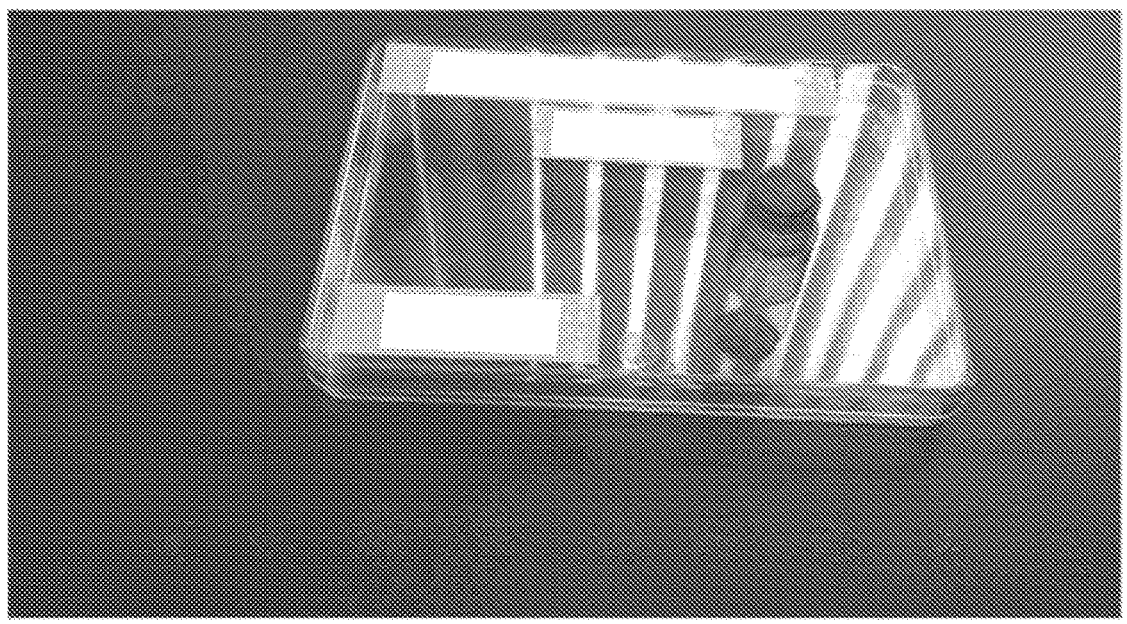
FIG. 15 is an image illustrating the applicator produced using the marker composition of Working Example 11 and the piece of paper to which the marker composition of Working Example 11 has been applied, in a state without irradiation of imaging light.
Figure 16:
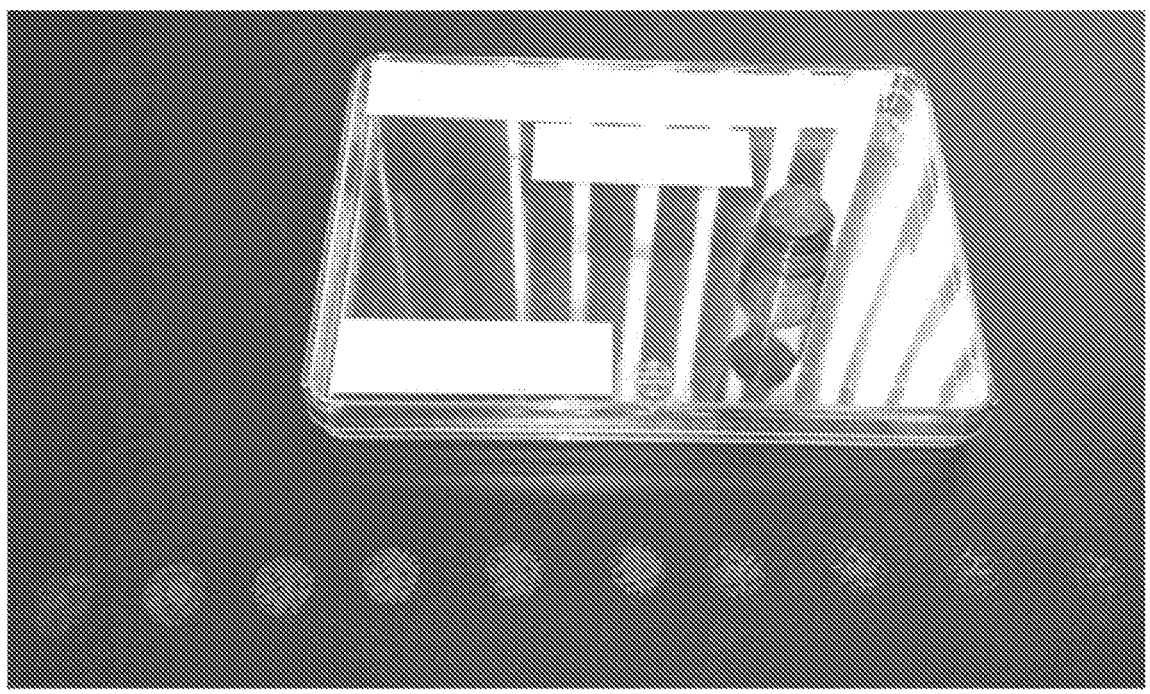
FIG. 16 is an image illustrating the applicator produced using the marker composition of Working Example 11 and the piece of paper to which the marker composition of Working Example 11 has been applied, in a state with irradiation of imaging light.
Figure 17:
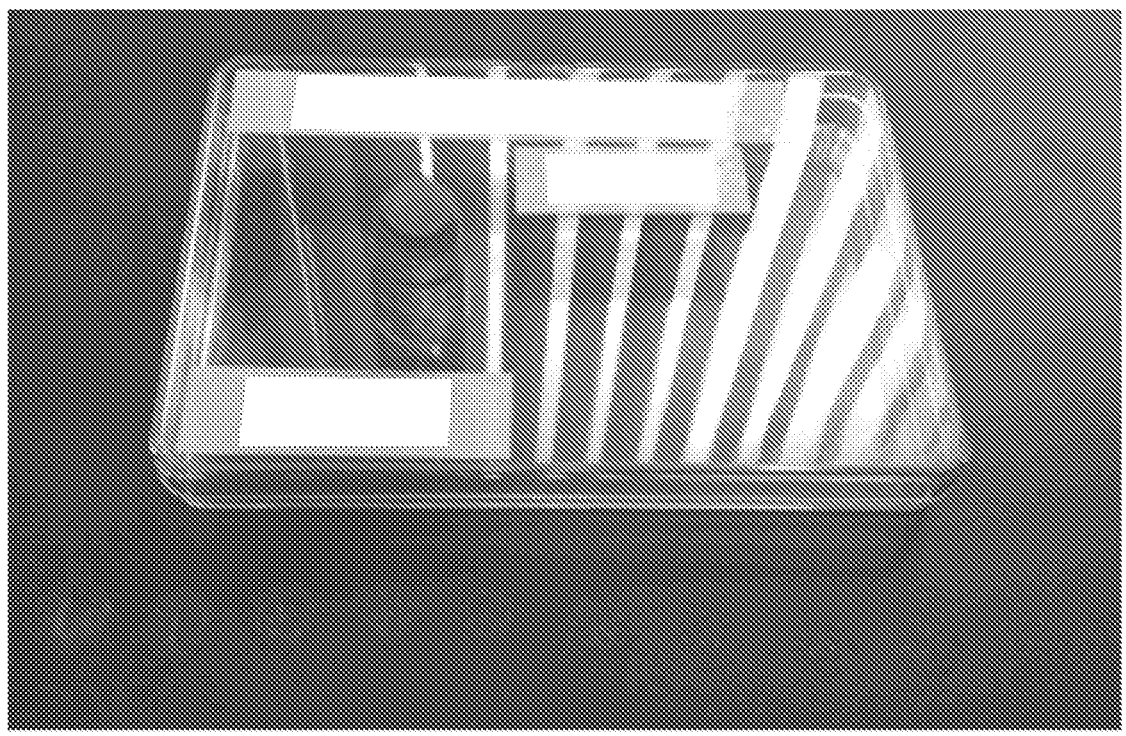
FIG. 17 is an image illustrating the applicator produced using the marker composition of Working Example 12 and the piece of paper to which the marker composition of Working Example 12 has been applied, in a state without irradiation of imaging light.
Figure 18:
FIG. 18 is an image illustrating the applicator produced using the marker composition of Working Example 12 and the piece of paper to which the marker composition of Working Example 12 has been applied, in a state with irradiation of imaging light.
Figure 19:
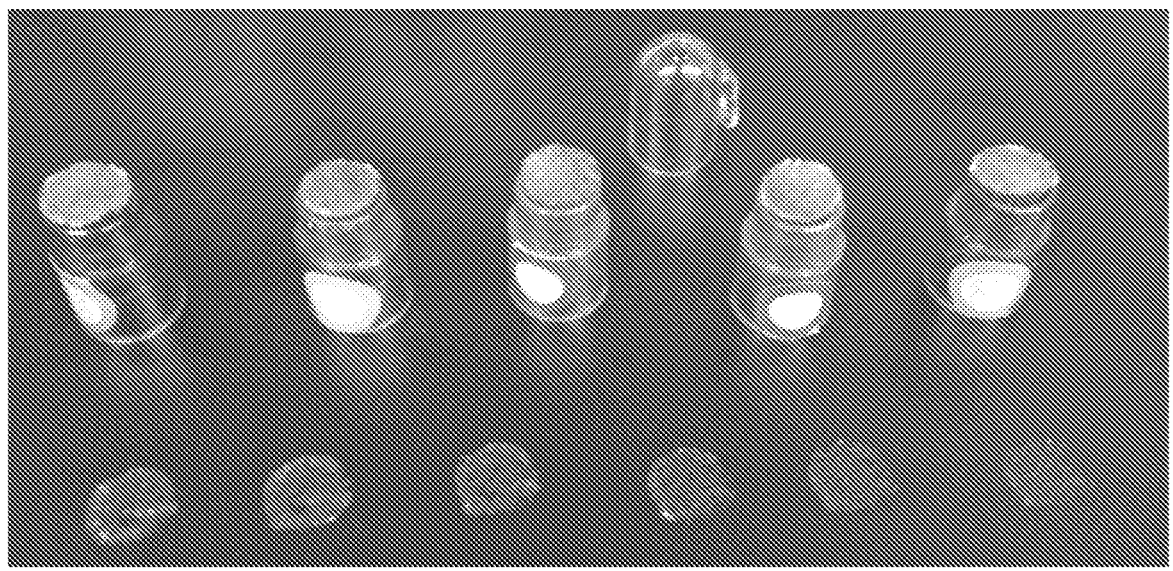
FIG. 19 is an image illustrating the applicator produced using the marker composition of Working Example 13 and the piece of paper to which the marker composition of Working Example 13 has been applied, in a state without irradiation of imaging light.
Figure 20:
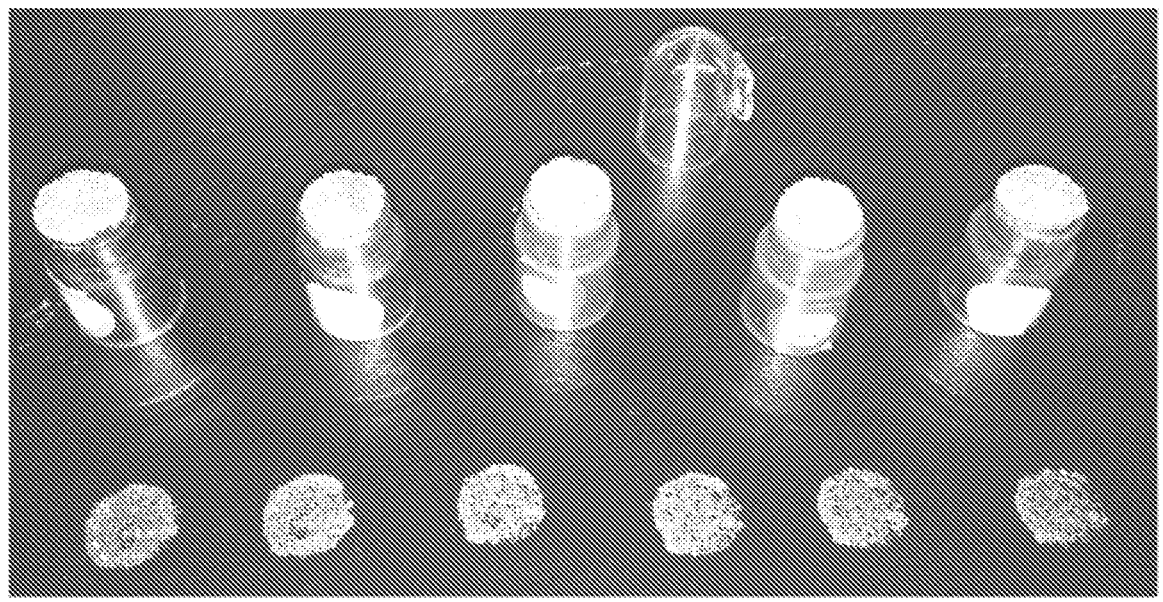
FIG. 20 is an image illustrating the applicator produced using the marker composition of Working Example 13 and the piece of paper to which the marker composition of Working Example 13 has been applied, in a state with irradiation of imaging light.

The obtained results are shown in Table 7. Moreover, for the applicator produced using the marker composition of Working Example 11 and the piece of paper coated using the marker composition of Working Example 11, an image illustrating the state when not illuminated by imaging light is illustrated in FIG. 15, and an image illustrating the state when illuminated by imaging light is illustrated in FIG. 16. Moreover, for the applicator produced using the marker composition of Working Example 12 and the piece of paper coated using the marker composition of Working Example 12, an image illustrating the state when not illuminated by imaging light is illustrated in FIG. 17, and an image illustrating the state when illuminated by imaging light is illustrated in FIG. 18. Moreover, for the applicator produced using the marker composition of Working Example 13 and the piece of paper coated using the marker composition of Working Example 13, an image illustrating the state when not illuminated by imaging light is illustrated in FIG. 19, and an image illustrating the state when illuminated by imaging light is illustrated in FIG. 20. In FIGS. 15 to 20 each of the multiple transfers of the marker composition of Working Examples 11 to 13 was made using the same respective applicator. Regarding visibility and reflectivity, there is essentially no difference between the evaluation results obtained when the applied marker composition was observed with the naked eye and the evaluation results based on images.

TABLE 7

| | | | Embodiment | | |
|---|---|---|---|---|---|
| | Material | 10 | 11 | 12 | 13 |
| particles | UB-24M | 70 | 70 | 70 | 70 |
| a dispersion medium; | Pluronic 25R4 | 30 | — | — | — |
| | Pluronic P84 | — | 30 | — | — |
| | Pluronic P103 | — | — | 30 | — |
| | Poloxamer 188 | — | — | — | 30 |
| Rating | state of the composition (25° C.) | paste | paste | paste | wax |
| | retention ability | A | A | A | A |
| | application property | A | B | B | C |
| | visibility | B | B | B | B |
| | reflectivity | A | A | A | A |
| | ease of wiping off | A | A | A | A |
| | stability | B | A | A | A |
| | ease of replacement | A | A | A | A |
| | recoating ability | A | A | A | A |

Next, when the temperature of the piece of paper was 40° C., 30° C., 20° C., or 4° C., the each marker composition of Working Examples 11 to 13 was applied three times to a white piece of paper. The application ability of the marker compositions on the piece of paper at each temperature was then evaluated in accordance with the same evaluation criteria as those of Working Examples 8 and 9. In addition, the state of the marker composition on the piece of paper was evaluated using the following criteria.
(State of Marker Composition on Paper)
A: The marker composition is a solid.
B: The marker composition is somewhat liquid-like.

Figure 21:
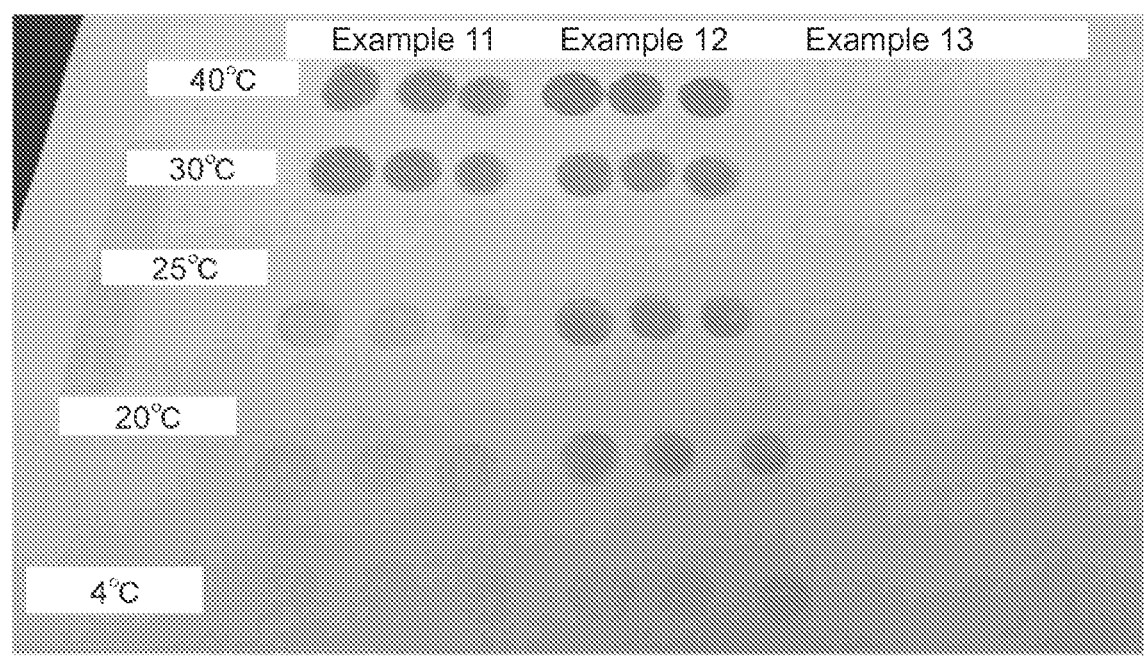
FIG. 21 is an image illustrating the piece of paper to which the marker compositions of Working Examples 11 to 13 have been applied, in a state without irradiation of imaging light.
Figure 22:
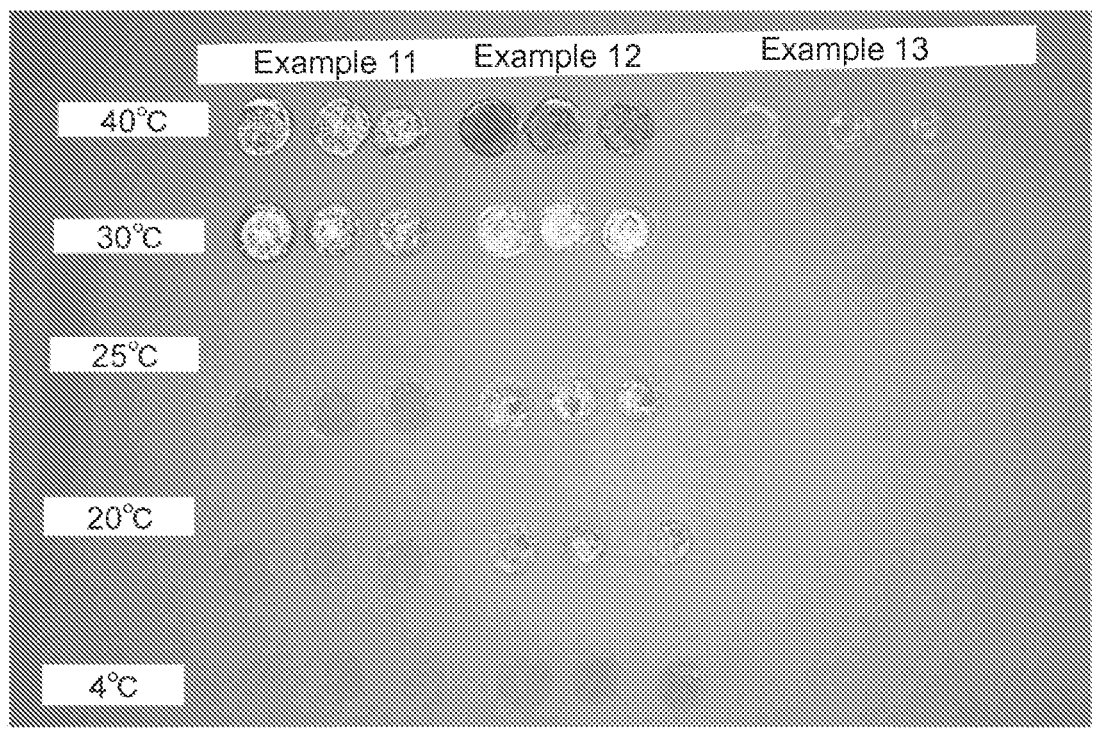
FIG. 22 is an image illustrating the piece of paper to which the marker compositions of Working Examples 11 to 13 have been applied, in a state with irradiation of imaging light.

The evaluation results are shown in Table 8. Moreover, for the paper to which the marker compositions of Working Examples 11 to 13 had been applied, an image of the state when not illuminated by imaging light is illustrated in FIG. 21, and an image of the state when illuminated by imaging light is illustrated in FIG. 22. When the temperature of the piece of paper was 30° C., 25° C., 20° C., and 4° C., the marker composition of Working Example 13 was hardly transferred to the piece of paper. The multiple transfers of the marker compositions in FIGS. 21 and 22 at each temperature in Working Examples 11 to 13 were made using the same respective applicator.

TABLE 8

| | | | Embodiment | | |
|---|---|---|---|---|---|
| | Material | | 11 | 12 | 13 |
| Rating | application property | 40° C. | A | A | B |
| | | 30° C. | A | A | C |
| | | 25° C. | B | A | C |
| | | 20° C. | B | A | C |
| | | 4° C. | B | B | C |
| | state on the piece of paper | 40° C. | B | B | A |
| | | 30° C. | B | B | — |
| | | 25° C. | A | B | — |
| | | 20° C. | A | B | — |
| | | 4° C. | A | A | — |

In the same manner as in Working Examples 8 and 9, applicator sets were produced using the marker composition of Working Example 10, except for change of the sponge to the sponge indicated in Table 9. The applicators of the obtained applicator sets were used to apply marker composition to pieces of paper. Then retention ability, application property, and stability were evaluated according to the same criteria as those of Working Examples 8 and 9. The obtained results are shown in Table 9.

TABLE 9

| Material | | Embodiment 10 | | | |
|---|---|---|---|---|---|
| | sponge | CFH-30 | CFH-40 | MF-50 | MF-55 |
| | cell count (no. per 25 mm) | 30 | 40 | 50 | 55 |
| Rating | retention ability | A | A | A | A |
| | application property | B | A | A | A |
| | stability | C | C | C | B |

Figure 23:
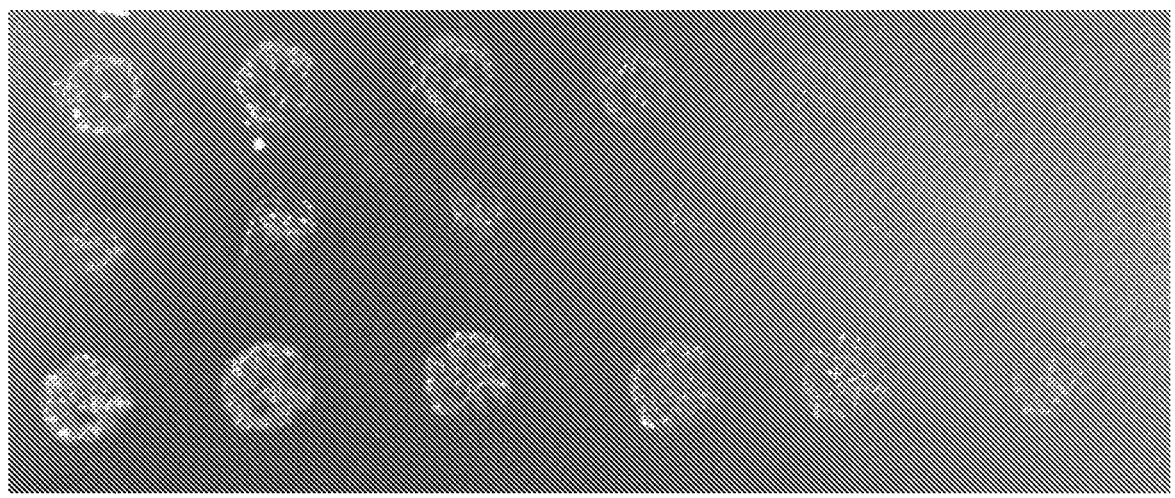
FIG. 23 is an image illustrating the piece of paper to which the marker composition of Working Example 13 has been applied, in a state without irradiation of imaging light.
Figure 24:
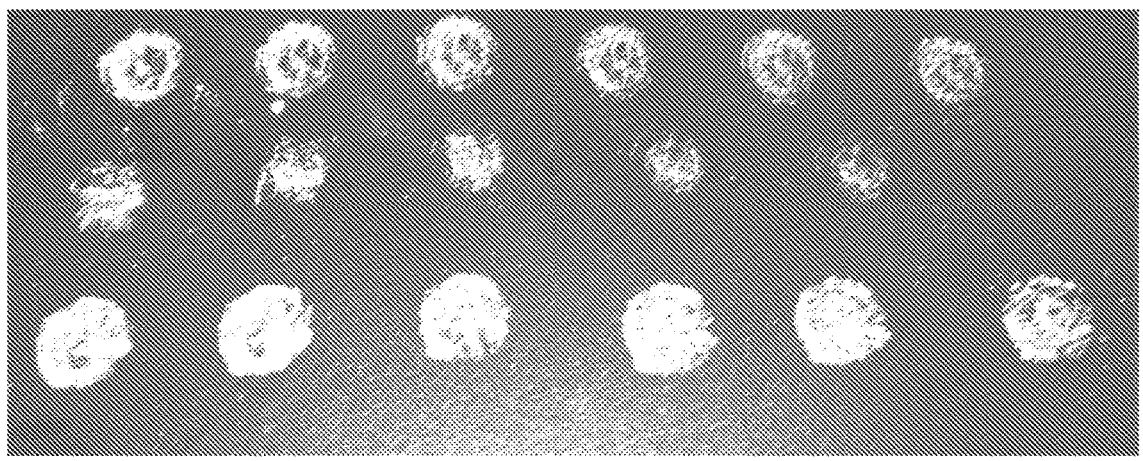
FIG. 24 is an image illustrating the piece of paper to which the marker composition of Working Example 13 has been applied, in a state with irradiation of imaging light.

In the same manner as in Working Examples 8 and 9, applicator sets were produced using the marker composition of Working Example 13, except for change of the sponge to the sponge indicated in Table 10. The applicators of the obtained applicator sets were used to apply marker composition to pieces of paper. Then retention ability, application property, and stability were evaluated according to the same criteria as those of Working Examples 8 and 9. The obtained results are shown in Table 10. Moreover, an image of pieces of paper to which the marker composition of Working Example 13 had been applied when MF-20, CFH-40, and MF-50 were used as the sponges is illustrated in FIG. 23 in a state in which the paper was not illuminated by imaging light, and an image of in the state in which the paper was illuminated by imaging light is illustrated in FIG. 24. Here, the upper row in FIGS. 23 and 24 shows results for CFH-40, the middle row shows results for MF-20, and the lower row shows results for MF-50. Each of the multiple transfers of the marker composition in FIGS. 23 and 24 was made using the same respective applicator.

TABLE 10

| Material | | Embodiment 13 | | | | |
|---|---|---|---|---|---|---|
| sponge | | MF-20 | MF-30 | CFH-30 | CFH-40 | MF-50 |
| cell count (no. per 25 mm) | | 20 | 30 | 30 | 40 | 50 |
| Rating | retention ability | A | A | A | A | B |
| | application property | C | B | B | A | A |
| | stability | C | A | A | A | A |

Working Examples 14 Through 23

<Preparation of the Marker Composition>

In Working Examples 14 to 23, marker compositions were prepared that included 70 parts by weight of UB-35M (produced by Unitika, Ltd., trade name) and 30 parts by weight of the dispersion medium having the composition shown in Table 11. The unit of the blended fractions of each of the materials in Table 11 is parts by weight. Furthermore, "PEG #600" in Table 11 is polyethylene glycol (produced by Wako Pure Chemical Industries, Ltd.), and "PPG #1400" is polypropylene glycol (produced by Wako Pure Chemical Industries, Ltd.). Moreover, the dispersion mediums included in the marker compositions of Working Examples 14 to 23 each had fluid points in the range of 0 to 60° C. For example, pour point of the dispersion medium included in the marker composition of Working Example 15 was 38° C.

<Production of Applicator Set, and Evaluation of Marker Composition Characteristics>

Respective applicator sets were produced using the marker compositions of Working Examples 14 to 23. The production procedure of the applicator sets was the same as that of Working Examples 8 and 9, except for use of MF-55 as the sponge. Thereafter, the applicators of the obtained applicator sets were used to apply the marker compositions of Working Examples 14 to 23 to white pieces of paper. The reflectivity of the marker composition and the state of the marker composition on the piece of paper at a paper temperature of 40° C., 30° C., 25° C., 20° C., and 4° C. were then evaluated in accordance with the same evaluation criteria as in Working Examples 8 to 13.

Figure 25:
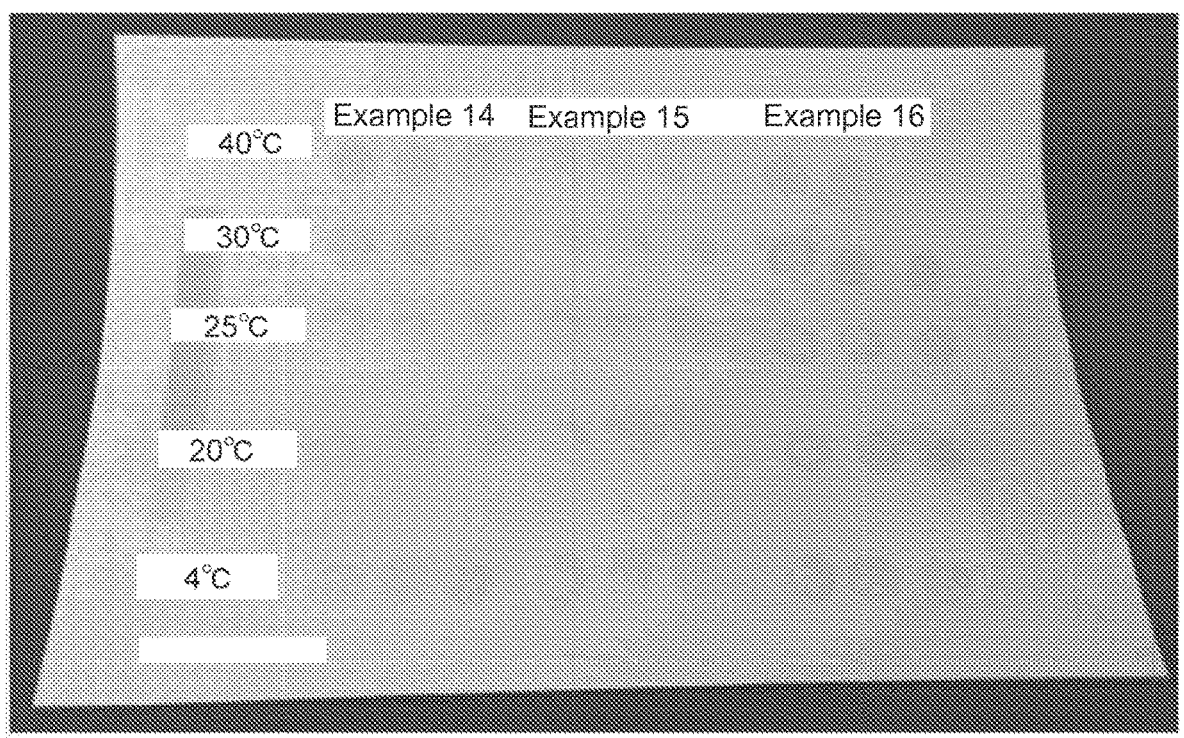
FIG. 25 is an image illustrating the piece of paper to which the marker compositions of Working Examples 14 to 16 have been applied, in a state without irradiation of imaging light.
Figure 26:
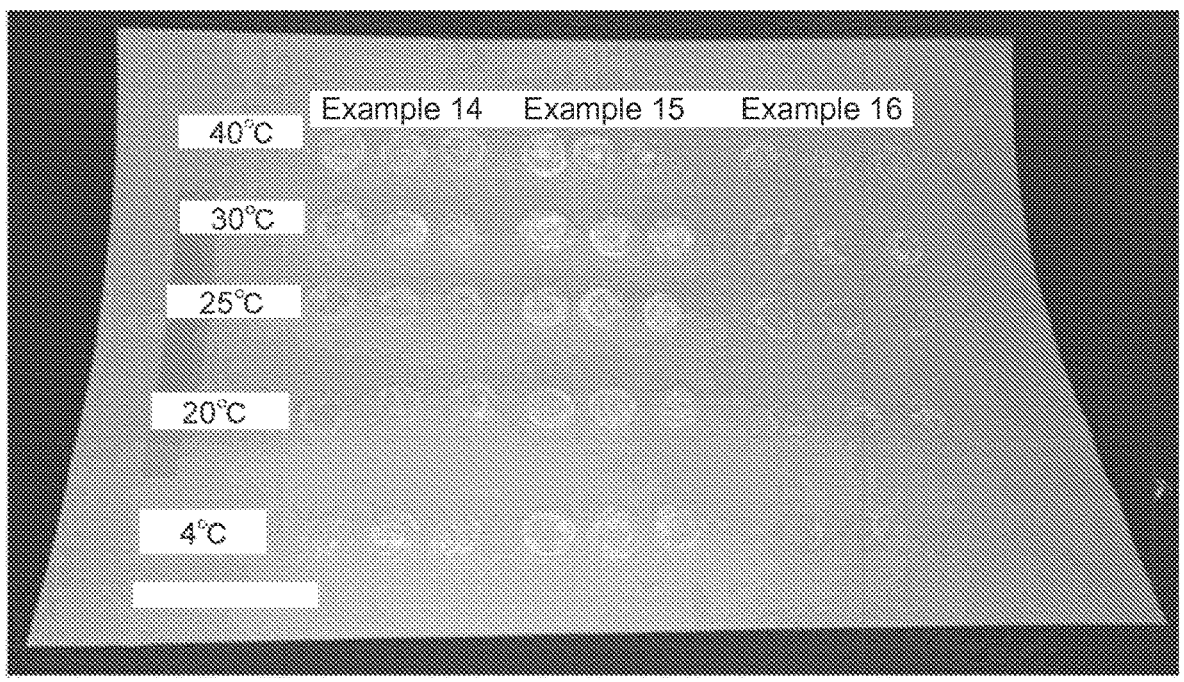
FIG. 26 is an image illustrating the piece of paper to which the marker compositions of Working Examples 14 to 16 have been applied, in a state with irradiation of imaging light.
Figure 27:
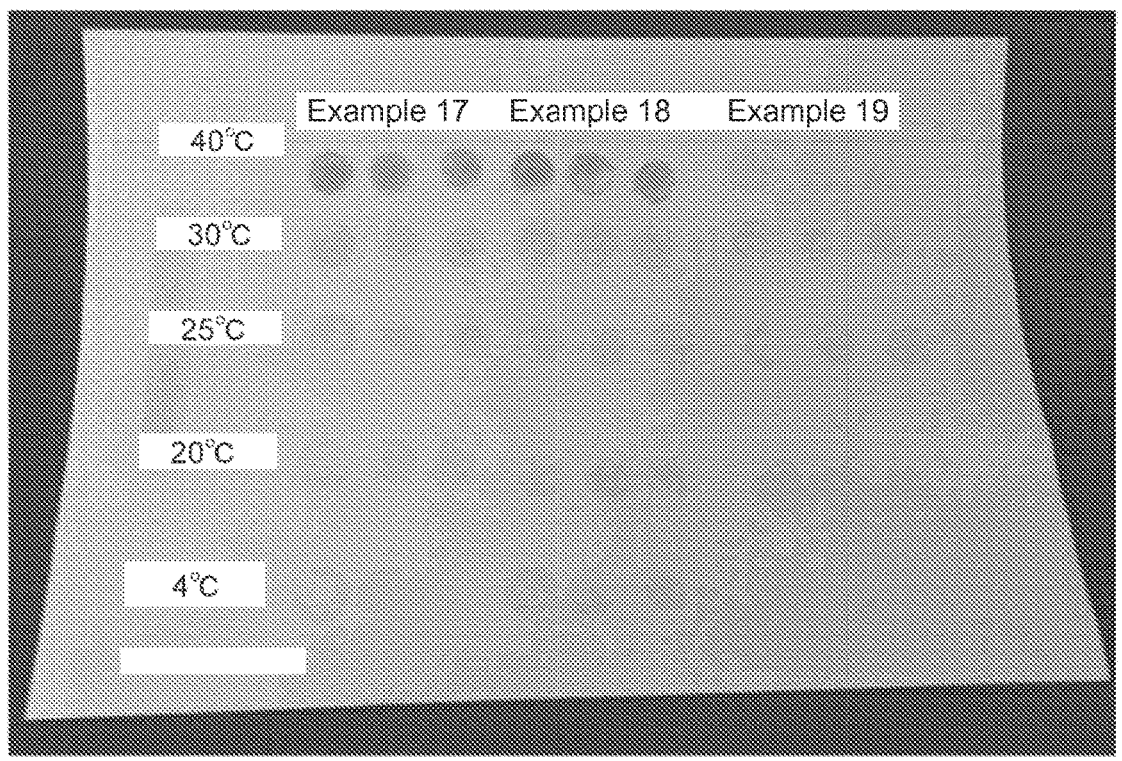
FIG. 27 is an image illustrating the piece of paper to which the marker compositions of Working Examples 17 to 19 have been applied, in a state without irradiation of imaging light.
Figure 28:
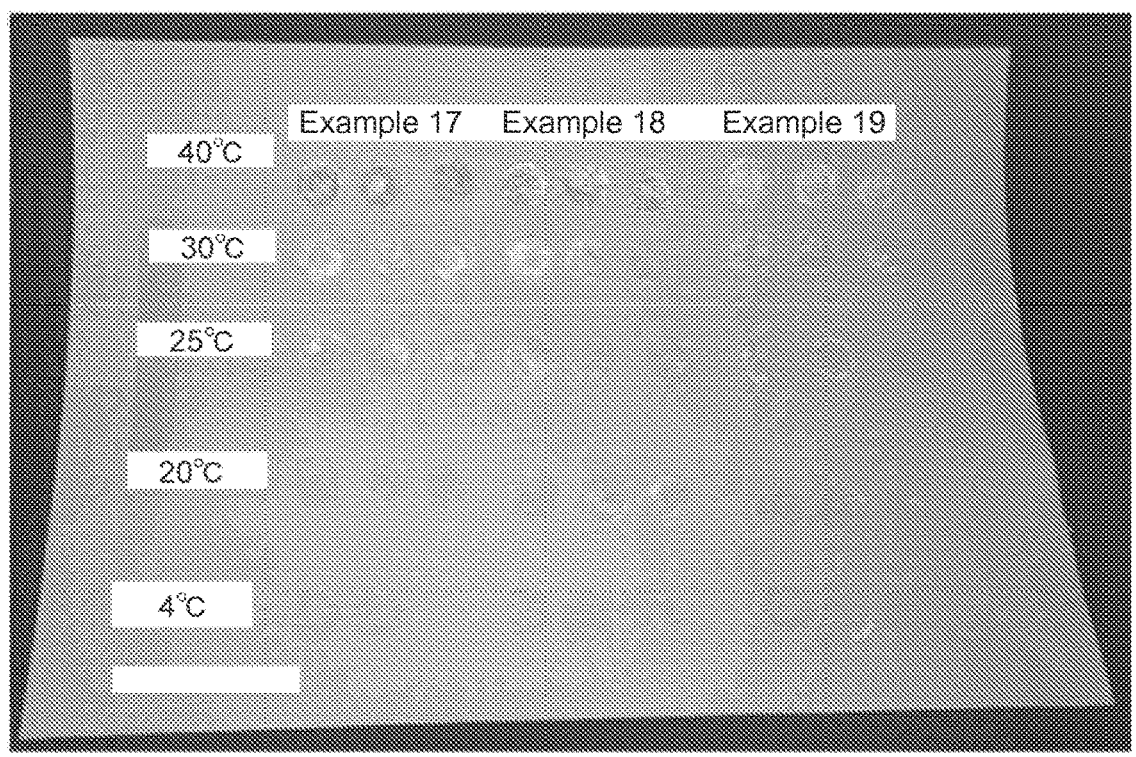
FIG. 28 is an image illustrating the piece of paper to which the marker compositions of Working Examples 17 to 19 have been applied, in a state with irradiation of imaging light.
Figure 29:
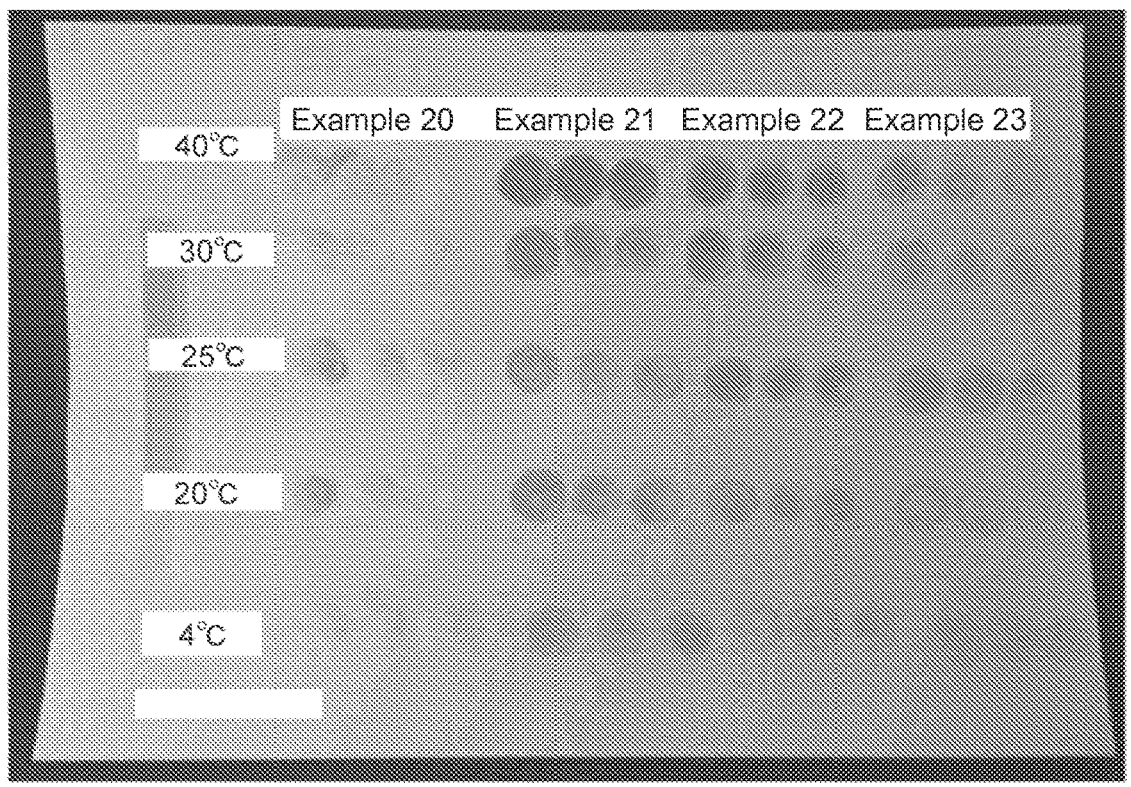
FIG. 29 is an image illustrating the piece of paper to which the marker compositions of Working Examples 20 to 23 have been applied, in a state without irradiation of imaging light.
Figure 30:
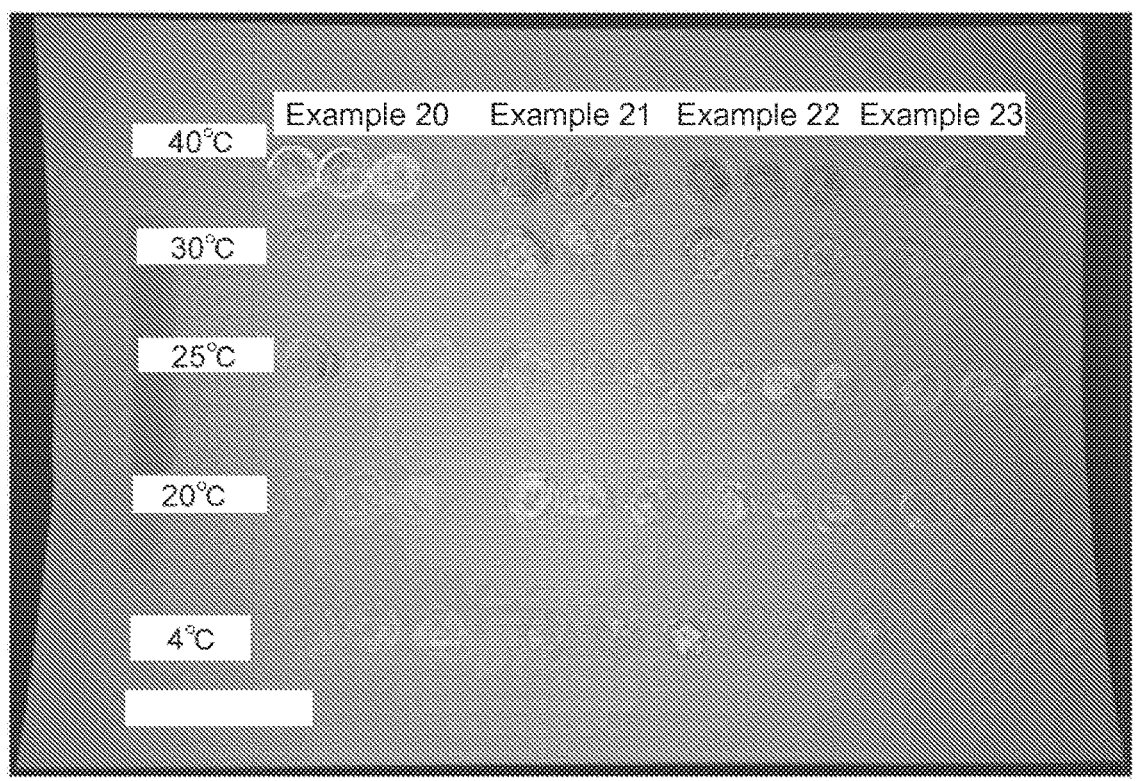
FIG. 30 is an image illustrating the piece of paper to which the marker compositions of Working Examples 20 to 23 have been applied, in a state with irradiation of imaging light.

The obtained results are shown in Table 11. Moreover, for the paper to which the marker compositions of Working Examples 14 to 16 had been applied, an image of the state when not illuminated by imaging light is illustrated in FIG. 25, and an image of the state when illuminated by imaging light is illustrated in FIG. 26. Moreover, for the paper to which the marker compositions of Working Examples 17 to 19 had been applied, an image of the state when not illuminated by imaging light is illustrated in FIG. 27, and an image of the state when illuminated by imaging light is illustrated in FIG. 28. Moreover, for the paper to which the marker compositions of Working Examples 20 to 23 had been applied, an image of the state when not illuminated by imaging light is illustrated in FIG. 29, and an image of the state when illuminated by imaging light is illustrated in FIG. 30. In FIGS. 25 to 30 the multiple transfers of the marker compositions of Working Examples 14 to 23 at each temperature were made using the same respective applicator. Regarding visibility and reflectivity, there is essentially no difference between the evaluation results obtained when the applied marker composition was observed with the naked eye and the evaluation results based on images.

Figure 31:
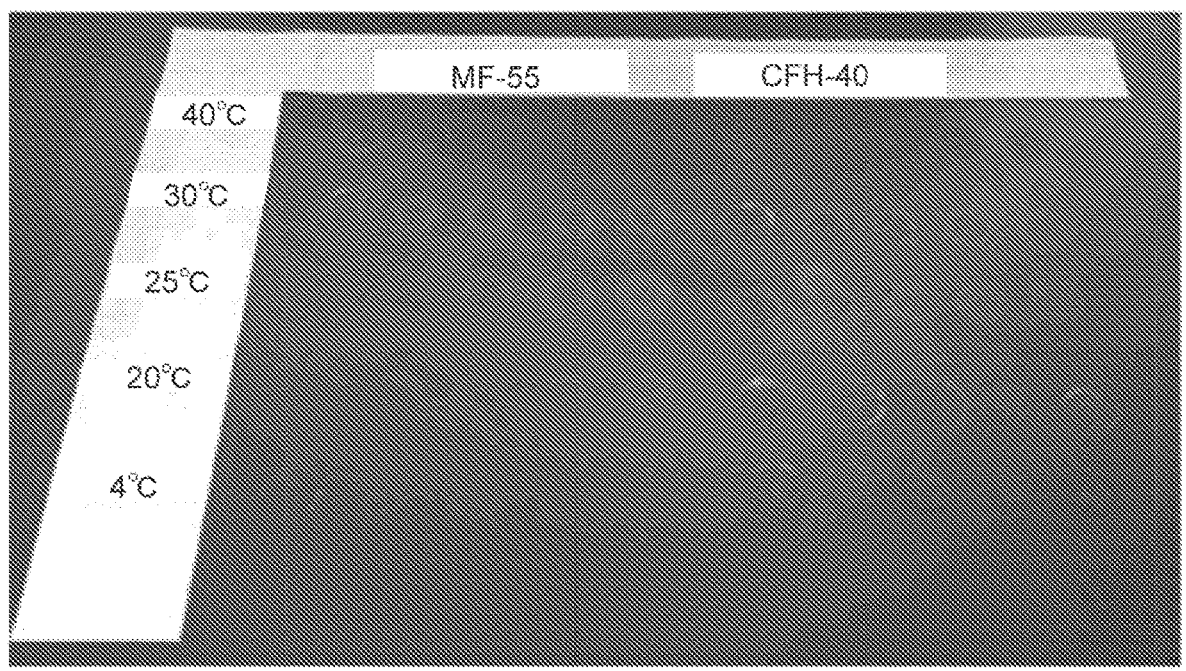
FIG. 31 is an image illustrating the piece of paper to which the marker composition of Working Example 15 has been applied, in a state without irradiation of imaging light.
Figure 32:
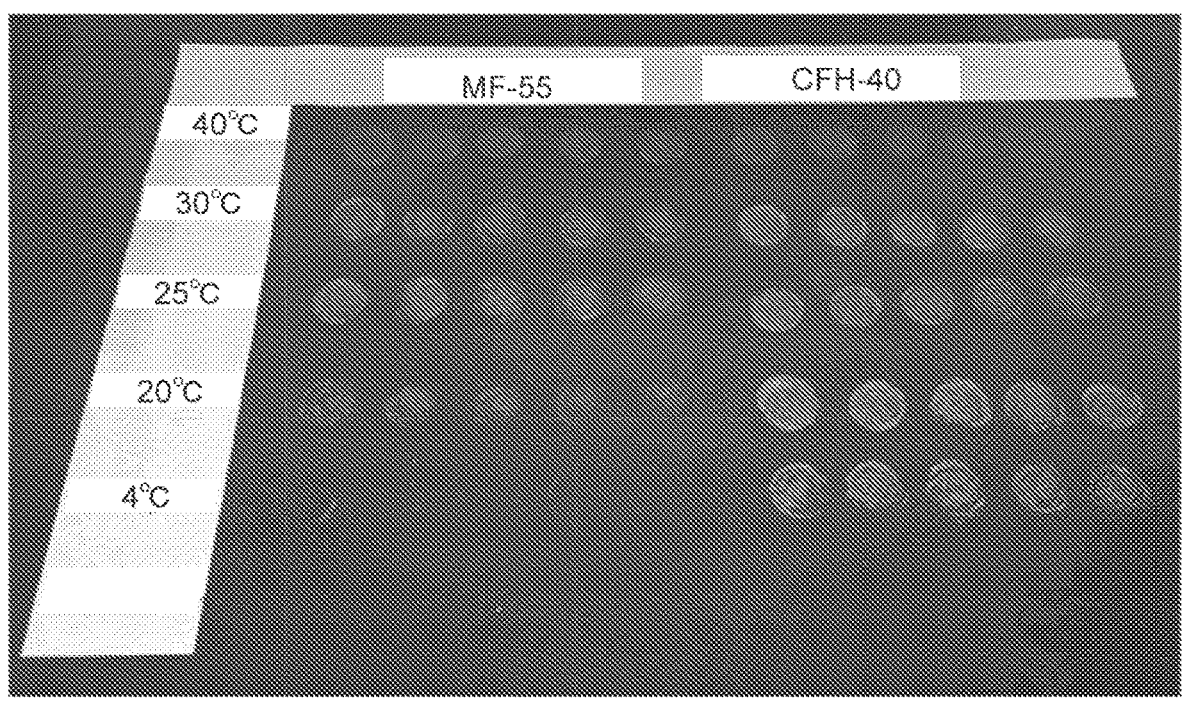
FIG. 32 is an image illustrating the piece of paper to which the marker composition of Working Example 15 has been applied, in a state with irradiation of imaging light.

Thereafter, the marker composition of Working Example 15 and the MF-55 and CFH-40 sponges were used to obtain applicator sets in the same manner as in Working Examples 8 and 9. Each of the applicators of the obtained applicator sets was used to apply marker composition 5 times onto black pieces of paper. The reflectivity of the marker composition and the state of the marker composition on the piece of paper at a paper temperature of 40° C., 30° C., 25° C., 20° C., and 4° C. were then evaluated in accordance with the same evaluation criteria as in Working Examples 8 to 13. The obtained results are shown in Table 12. Moreover, for the pieces of paper to which the composition of Working Examples 15 had been applied using the applicator having the MF-55 and CFH-40 sponges, FIG. 31 shows the state in which the paper is not illuminated by imaging lighting, and FIG. 32 shows the state in which the paper is illuminated by imaging lighting. The multiple transfers of the marker compositions at each temperature and for each sponge in FIGS. 31 to 32 were made using the same respective applicator. Regarding visibility and reflectivity, there is essentially no difference between the evaluation results obtained when the applied marker composition was observed with the naked eye and the evaluation results based on images.

TABLE 11

| a dispersion medium; | | Embodiment | | | | | | | | | |
|---|---|---|---|---|---|---|---|---|---|---|---|
| | | 14 | 15 | 16 | 17 | 18 | 19 | 20 | 21 | 22 | 23 |
| Poloxamer 188 | | 90 | 70 | 90 | 95 | 90 | 95 | 50 | 25 | 50 | 75 |
| Pluronic P103 | | — | — | — | — | — | — | — | 75 | 50 | 25 |
| softening | glycerin | 10 | 30 | — | — | — | — | 50 | — | — | — |
| agent | PEG#600 | — | — | 10 | 5 | — | — | — | — | — | — |
| | PPG#4000 | — | — | — | — | 10 | 5 | — | — | — | — |
| Rating | state of the composition (25° C.) | wax | wax | wax | wax | wax | wax | wax | wax | wax | wax |
| | reflectivity 4° C. | B | B | C | C | C | C | B | B | B | B |
| | 20° C. | B | A | C | C | C | C | B | A | A | B |
| | 25° C. | B | A | C | C | C | C | B | A | A | A |
| | 30° C. | A | A | B | A | A | B | B | A | A | A |
| | 40° C. | A | A | B | A | A | A | A | A | A | A |
| | state on the 4° C. | A | B | A | A | A | A | A | B | A | A |
| | piece of paper 20° C. | A | A | A | A | A | A | A | B | B | A |
| | 25° C. | A | A | B | B | B | A | A | B | B | B |
| | 30° C. | A | A | B | B | B | A | A | B | B | B |
| | 40° C. | A | A | B | B | B | A | A | B | B | B |

TABLE 12

| | Material | | Embodiment 15 | |
|---|---|---|---|---|
| | sponge | | MF-55 | CFH-40 |
| Rating | reflectivity | 4° C. | B | A |
| | | 20° C. | A | A |
| | | 25° C. | A | A |
| | | 30° C. | A | A |
| | | 40° C. | A | A |
| | state on the piece of paper | 4° C. | B | A |
| | | 20° C. | A | A |
| | | 25° C. | A | A |
| | | 30° C. | A | A |
| | | 40° C. | A | A |

The obtained results are shown in Table 13.

TABLE 13

| Material | | Embodiment | | | |
|---|---|---|---|---|---|
| | | 24 | 25 | 26 | 27 |
| particles UB-35M | | 60 | 70 | 75 | 80 |
| a dispersion medium; | | 40 | 30 | 25 | 20 |
| Rating | state of the composition (25° C.) | wax | wax | wax | wax |
| | retention ability | A | A | A | B |
| | reflectivity 4° C. | C | C | A | B |
| | 25° C. | A | A | A | A |
| | 40° C. | B | B | A | A |
| | ease of wiping off | B | A | A | A |

Working Examples 24 Through 27

<Preparation of the Marker Composition>

In Working Examples 24 to 27, marker compositions having the compositions indicated in Table 13 were prepared using UB-35M (produced by Unitika Ltd., trade name) and the dispersion mediums of Working Example 15 indicated in Table 11. The unit of the blended fractions of each of the materials in Table 13 is parts by weight.

<Production of Applicator Set, and Evaluation of Marker Composition Characteristics>

Respective applicator sets were produced using the marker compositions of Working Examples 24 to 27. The production procedure for the applicator sets is the same as in the case of Working Examples 8 and 9 with the exception of changing the sponge to CFH-40. At this time, the retention ability of the sponge of the marker composition was evaluated in accordance with the same evaluation criteria as in Working Examples 8 and 9. Next, the temperatures of the applicators of the obtained applicator sets were set to 40° C., 25° C., or 4° C., and the marker compositions of Working Examples 24 to 27 were applied to pieces of paper. The reflectivity of the marker compositions was evaluated in accordance with the same evaluation criteria as in Working Examples 8 and 9.

Further, the marker compositions of Working Examples 24 to 27 were applied to the surfaces of stainless steel materials (SUS) at 25° C. using the obtained applicators. The ease of wiping the marker compositions off the SUS surface was then evaluated in accordance with the same evaluation criteria as in Working Examples 8 to 13.

INDUSTRIAL APPLICABILITY

The applicator, the applicator set, the degree of cleanliness determination method, and the degree of cleanliness determination system of the present invention are useful for the determination of the degree of cleanliness at hospitals and other facilities, for example.

REFERENCE NUMERALS 30, 40, 50, 60, 70, 80, 110, 120, 130, 140, 150, 160 applicator
32, 42, 52, 62, 72, 82, 112, 122, 132, 142, 152, 162 applicator body
34, 44, 54, 64, 74, 84, 114, 124, 134, 144, 154, 164 retention body
34a male thread part
36, 116, 126, 136, 146, 156, 166 lid body
36a female thread part
38, 45, 55, 65, 75, 85, 118, 128, 138, 148, 158, 168 sealing component
46, 56, 66, 76, 86 retention part
48, 58, 68, 78, 88 lid part
90 lid body
100,200 applicator set
170 fixing member

What is claimed is:

1. An applicator comprising:
   a marker composition containing retroreflective particles and a dispersion medium, a blending ratio of the retroreflective particles being from 50 to 90 mass % on the basis of the total marker composition; wherein the dispersion medium comprises a water-soluble polymer, and an applicator body capable of retaining the marker composition;

wherein an exposed part of the applicator body is capable of delivering the marker composition to a surface of an application target surface to be cleaned.

2. The applicator of claim 1, wherein the applicator body is porous.

3. The applicator of claim 1, wherein the applicator body has interconnected cells in the interior of the applicator body.

4. The applicator of claim 3, wherein the cell count of the interconnected cells is 15 to 100 cells per 25 mm.

5. The applicator of claim 1, further comprising:
a retention body for retaining the applicator body so that at least part of the applicator body is exposed;
and a lid body detachably attached to the retention body, for hermetically sealing the exposed part of the applicator body.

6. An applicator set comprising a plurality of the applicators of claim 1,
each applicator respectively comprising:
a retention body for retention of the applicator body, the retention body retaining the applicator body so that at least part of the applicator body is exposed,
and a lid part detachably attached to the retention part of another applicator, the lid part being capable of hermetically sealing the exposed part of the applicator body of the other applicator.

7. The applicator set of claim 6, wherein a single applicator among the plurality of applicators is capable of being distinguished from the other applicators.

8. A method for determining a degree of cleanliness, the method comprising:
applying the marker composition to a surface to be cleaned using the applicator according to claim 1;
cleaning the surface;
irradiating light onto the surface;
sensing a reflected light from the retroreflective particles; and
determining a degree of cleanliness based on the result of sensing of the reflected light.

9. A system for determining a degree of cleanliness, the system comprising:
the applicator according to claim 1;
a sensing means for sensing reflected light from retroreflective particles based on image data showing a condition of a surface to be cleaned; and
a determination means for determining of degree of cleanliness of the surface to be cleaned based on results of sensing the reflected light obtained by the sensing means.

10. The applicator of claim 1, wherein the marker composition further comprises water, wherein the water is present in the marker composition at 3-25% by weight.

11. The applicator of claim 1, wherein the marker composition further comprises an alcohol, wherein the alcohol is present in the marker composition at 4-16% by weight.

12. The applicator of claim 1, wherein the marker composition further comprises a humectant, wherein the humectant is present in the marker composition at 0.1-2% by weight.

13. The applicator of claim 1, wherein the marker composition further comprises a pH adjusting agent.

14. The applicator of claim 1, wherein the marker composition further comprises a surfactant.

15. The applicator of claim 14 wherein the marker composition, when dried, retains its water-dispersibility.

* * * * *